US012120266B2

(12) United States Patent
Gaddam et al.

(10) Patent No.: US 12,120,266 B2
(45) Date of Patent: Oct. 15, 2024

(54) PROVIDING HEALTH URGENCY CONTEXT FOR INCOMING CALLS

(71) Applicant: Optum, Inc., Minnetonka, MN (US)

(72) Inventors: Ramprasad Anandam Gaddam, Mumbai (IN); Gregory J. Boss, Saginaw, MI (US); Jon Kevin Muse, Thompsons Station, TN (US); Kristine Xu, Stoneham, MA (US)

(73) Assignee: OPTUM, INC., Minnetonka, MN (US)

( * ) Notice: Subject to any disclaimer, the term of this patent is extended or adjusted under 35 U.S.C. 154(b) by 441 days.

(21) Appl. No.: 17/499,273

(22) Filed: Oct. 12, 2021

(65) Prior Publication Data

US 2023/0114424 A1    Apr. 13, 2023

(51) Int. Cl.
| | |
|---|---|
| *H04M 3/00* | (2024.01) |
| *A61B 5/0205* | (2006.01) |
| *A61B 5/021* | (2006.01) |
| *A61B 5/024* | (2006.01) |
| *A61B 5/145* | (2006.01) |
| *A61B 5/16* | (2006.01) |
| *H04M 3/436* | (2006.01) |
| *H04W 4/16* | (2009.01) |

(52) U.S. Cl.
CPC ......... *H04M 3/4365* (2013.01); *A61B 5/0205* (2013.01); *A61B 5/021* (2013.01); *A61B 5/024* (2013.01); *A61B 5/14532* (2013.01); *A61B 5/14542* (2013.01); *A61B 5/165* (2013.01); *H04W 4/16* (2013.01)

(58) Field of Classification Search
CPC .................................................. H04M 3/4365

USPC ......................................................... 455/415
See application file for complete search history.

(56) References Cited

U.S. PATENT DOCUMENTS

| | | |
|---|---|---|
| 6,574,484 B1 | 6/2003 | Carley |
| 8,538,375 B2 | 9/2013 | Franz et al. |
| 8,681,968 B2 | 3/2014 | Vendrow |
| 8,908,849 B2 | 12/2014 | Yin et al. |
| 9,351,133 B2* | 5/2016 | Offen .................. H04M 3/4365 |
| 9,794,402 B2* | 10/2017 | Dvortsov .............. H04W 4/027 |
| 9,838,858 B2 | 12/2017 | Anand et al. |
| 10,554,814 B1* | 2/2020 | Srivastava ............ H04M 1/575 |
| 10,805,786 B2 | 10/2020 | Pellegrini et al. |
| 11,233,897 B1* | 1/2022 | Gardner ................ H04W 12/06 |
| 2006/0246881 A1* | 11/2006 | Winkler .................. H04M 1/64 455/415 |

(Continued)

OTHER PUBLICATIONS

Genes, et al., "From smartphone to EHR: a case report on integrating patient-generated health data," NPJ digital medicine 1, No. 1, Jun. 20, 2018, 6 pp.

(Continued)

*Primary Examiner* — Qutbuddin Ghulamali
(74) *Attorney, Agent, or Firm* — Shumaker & Sieffert, P.A.

(57) ABSTRACT

A computing device may receive, from a remote computing device, a request to establish a communication session with the remote computing device and contextual information indicative of an urgency level of the communication session. The computing device may output, at one or more output devices, the contextual information indicative of the urgency level of the communication session and at least one of: haptic output or an audible alert that indicates the request to establish the communication session.

18 Claims, 11 Drawing Sheets

(56) References Cited

U.S. PATENT DOCUMENTS

| | | | |
|---|---|---|---|
| 2014/0171038 A1* | 6/2014 | Singvall | H04M 3/42195 |
| | | | 455/414.1 |
| 2014/0273912 A1 | 9/2014 | Peh et al. | |
| 2014/0357215 A1 | 12/2014 | Michaelis et al. | |
| 2015/0220696 A1* | 8/2015 | Lekutai | G16H 15/00 |
| | | | 705/2 |
| 2015/0312392 A1* | 10/2015 | Smereka | H04M 19/04 |
| | | | 455/415 |
| 2023/0114424 A1* | 4/2023 | Gaddam | A61B 5/14532 |
| | | | 455/415 |
| 2024/0007560 A1* | 1/2024 | Drozhilkin | H04M 3/58 |

OTHER PUBLICATIONS

Paredes, et al., "SOSPhone: a mobile application for emergency calls," University Access in the Information Society 13, No. 3, Aug. 2014, 14 pp.

"Public Safety Internet of Things (IoT) Use Case Report and Assessment Attributes," NPSTC, Jun. 2019, 65 pp.

* cited by examiner

PROVIDING HEALTH URGENCY CONTEXT FOR INCOMING CALLS

BACKGROUND

A computing device, such as smartphone, may implement a do not disturb feature that, when active, may silence incoming calls. That is, when a computing device receives an incoming call while the do not disturb feature is turned on, the computing device may refrain from ringing or vibrating to notify the user of the computing device of the incoming call. The computing device may provide exceptions to the do not disturb feature to allow the computing device to ring or vibrate when the computing device receives certain incoming calls. For example, the computing device may determine a list of contacts that are allowed to bypass the do not disturb feature. When the computing device receives an incoming call from a contact in such a list of contacts, the computing device may allow the incoming call to bypass the do not disturb feature, and the computing device may ring or vibrate to notify the user of the incoming call.

SUMMARY

In general, techniques of this disclosure are directed techniques for a computing device to determine whether to enable a request to establish a communication session, such as an incoming call, to bypass a do not disturb feature that is active at the computing device based on an urgency level of the communication session. If the computing device determines that the urgency level of the communication session meets a do not disturb exception, the computing device may enable the request to bypass the do not disturb feature to cause the computing device to output an audible alert and/or haptic output to indicate receipt of the request.

A computing device that sends a request to establish a communication session to a remote computing device may determine an urgency level of the communication session based on health information associated with the user of the computing device. The computing device may use sensors to measure health parameters of the user of the computing device, such as the stress level of the user, and may determine, based on the health parameters of the user, the urgency level of the communication session. The computing device may therefore send the request to establish a communication session along with one or more of the health parameters and/or the urgency level of the communication session to a remote computing device, so that the computing device may output an indication of the request to establish the communication session along with indications of the health parameters of the user of the remote computing device and/or an indication of the urgency level of the communication session. When a do not disturb feature of the computing device is active, the remote device may determine, based on the urgency level of the communication session and/or the health parameters of the user, whether to enable the request to establish the communication session to bypass the do not disturb feature of the remote computing device.

The techniques of this disclosure may provide one or more technical advantages. By determining whether a request to establish a communication session can bypass a do not disturb feature based on the urgency level of the communication session, the techniques of this disclosure improves the do not disturb functionality of a computing device by enabling the computing device to adaptively refrain from silencing the computing device when the computing device receives a request to establish a communication session that is likely to be of interest to the user of the computing device. Adaptively refraining from silencing the computing device when the computing device receives a request to establish a communication session that is likely to be of interest to the user of the computing device may enable the user of the computing device to miss fewer requests to establish communication sessions that are likely to be of interest to the user of the computing device, thereby improving the functionality of the computing device.

In one example, this disclosure describes a method includes receiving, by the computing device from a remote computing device, a request to establish a communication session with the remote computing device and contextual information indicative of an urgency level of the communication session; and outputting, by the computing device, the contextual information indicative of the urgency level of the communication session and at least one of: haptic output or an audible alert that indicates the request to establish the communication session.

In another example, this disclosure describes a computing device includes one or more output devices; and one or more processors configured to: while a do not disturb feature of the computing device is active at the computing device, receive, from a remote computing device, a request to establish a communication session with the remote computing device and contextual information indicative of an urgency level of the communication session; and output, at the one or more output devices, the contextual information indicative of the urgency level of the communication session and at least one of: haptic output or an audible alert that indicates the request to establish the communication session.

In another example, this disclosure describes a computer-readable storage medium storing instructions that, when executed, cause one or more processors of a computing device to: receive, from a remote computing device, a request to establish a communication session with the remote computing device and contextual information indicative of an urgency level of the communication session; and output, at one or more output devices, the contextual information indicative of the urgency level of the communication session and at least one of: haptic output or an audible alert that indicates the request to establish the communication session.

In another example, this disclosure describes a method that includes receiving, by a computing device from one or more sensors, sensor data indicative of at least health information associated with a user of the computing device; in response to determining to send a request to establish a communication session to a remote computing device, determining, by the computing device and based at least in part on the health information associated with the user, contextual information indicative of an urgency level of the communication session; sending, by the computing device to the remote computing device, the request to establish the communication session and an indication of the urgency level of the communication session.

In another example, this disclosure describes a computing device that includes one or more sensors configured to sense at least health information associated with a user of the computing device; and one or more processors configured to: receive, from at least the one or more sensors, sensor data; in response to determining to send a request to establish a communication session to a remote computing device, determine, based at least in part on the health information associated with the user, contextual information indicative of an urgency level of the communication session; and send, to the remote computing device, the request to establish the communication session and an indication of the urgency level of the communication session.

In another example, this disclosure describes a computer-readable storage medium storing instructions that, when executed, cause one or more processors of a computing device to: receive, from one or more sensors, sensor data; in response to determining to send a request to establish a communication session to a remote computing device, determine, based at least in part on the health information associated with the user, contextual information indicative of an urgency level of the communication session; and send, to the remote computing device, the request to establish the communication session and an indication of the urgency level of the communication session.

The details of one or more examples are set forth in the accompanying drawings and the description below. Other features, objects, and advantages of the disclosure will be apparent from the description and drawings, and from the claims.

DETAILED DESCRIPTION

Figure 1A:
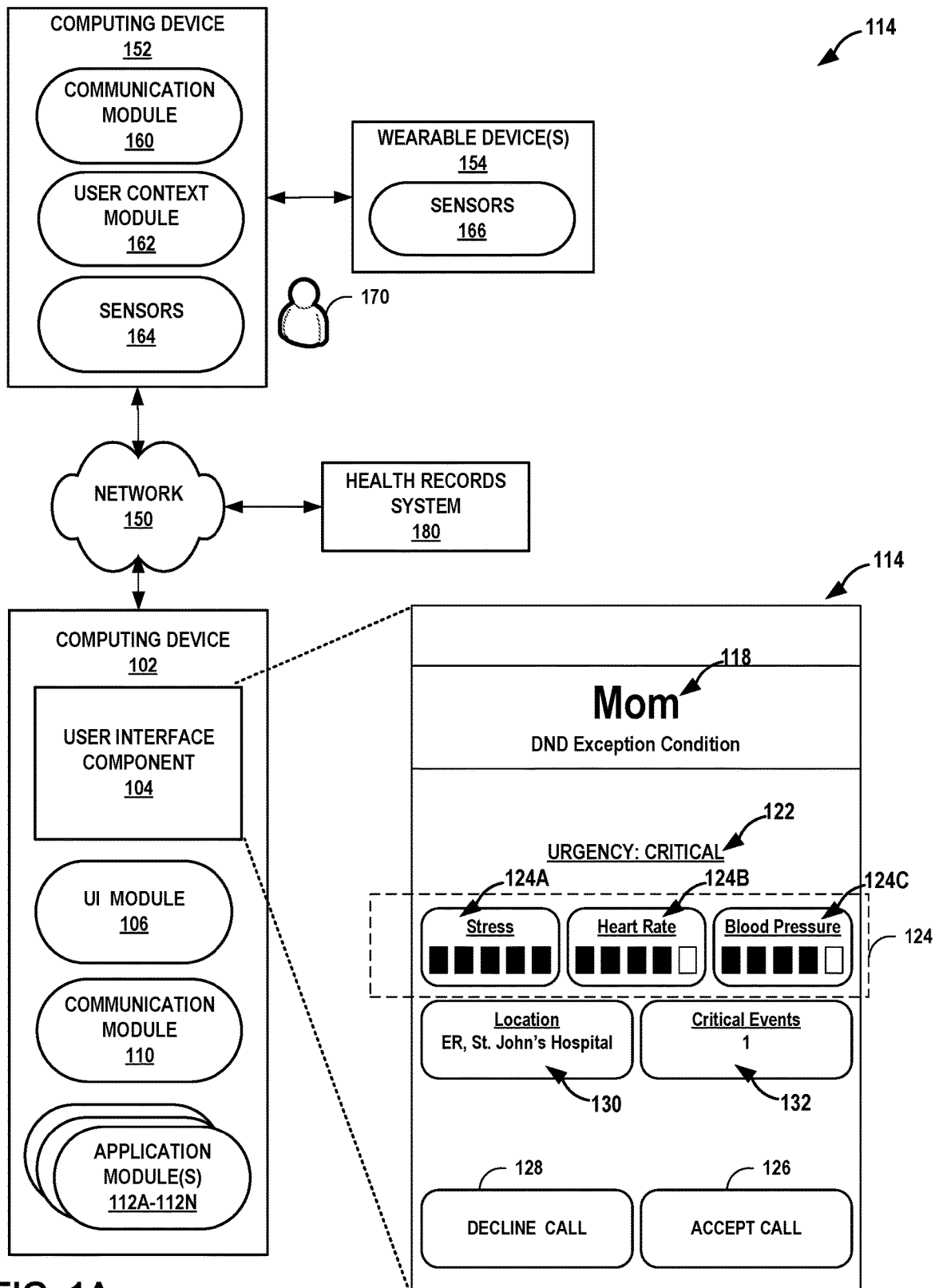
FIGS. 1A-1C are conceptual diagrams illustrating an example system for providing health urgency context for communicating between computing devices, in accordance with one or more aspects of the present disclosure.
Figure 1B:
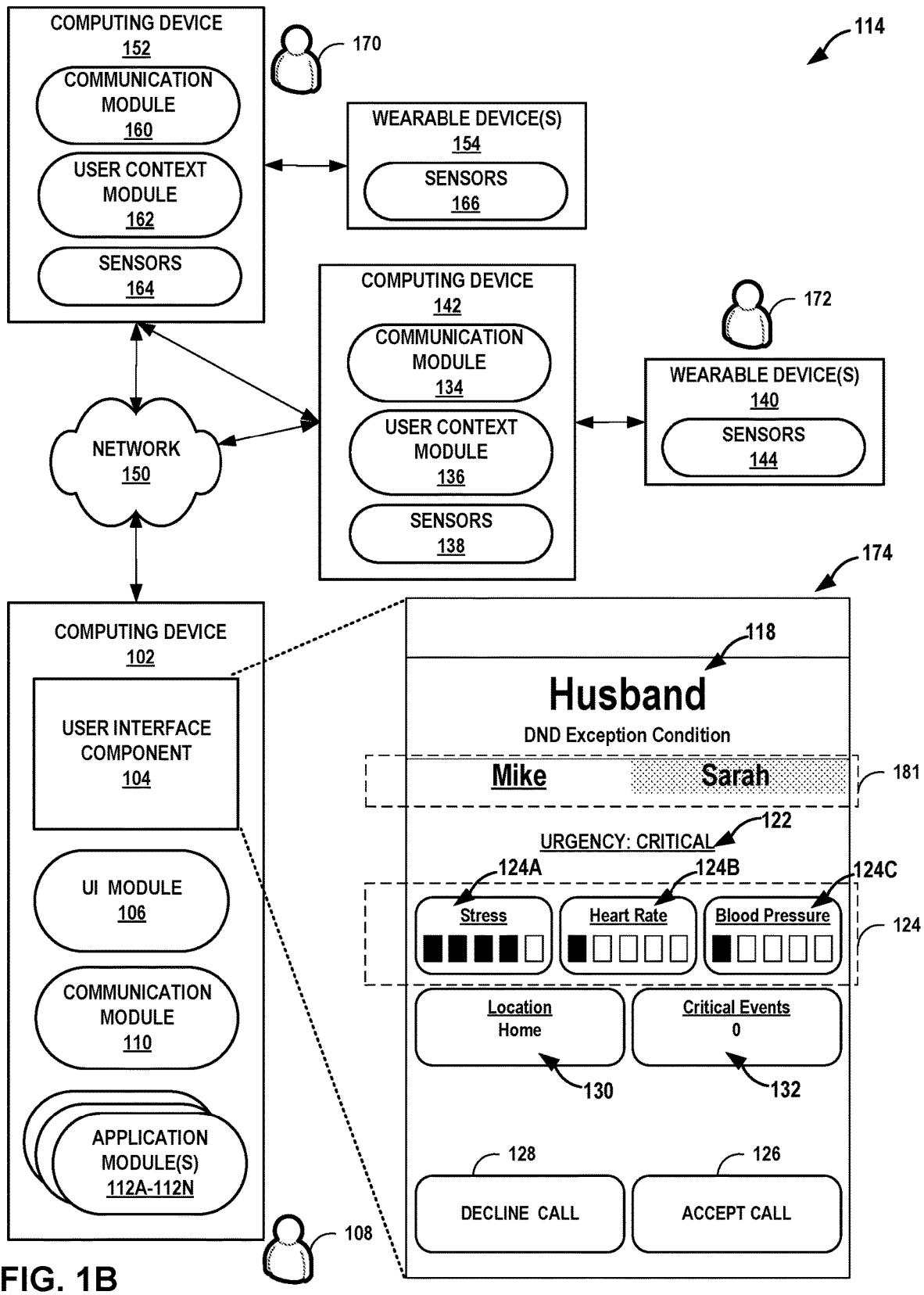
Figure 1C:
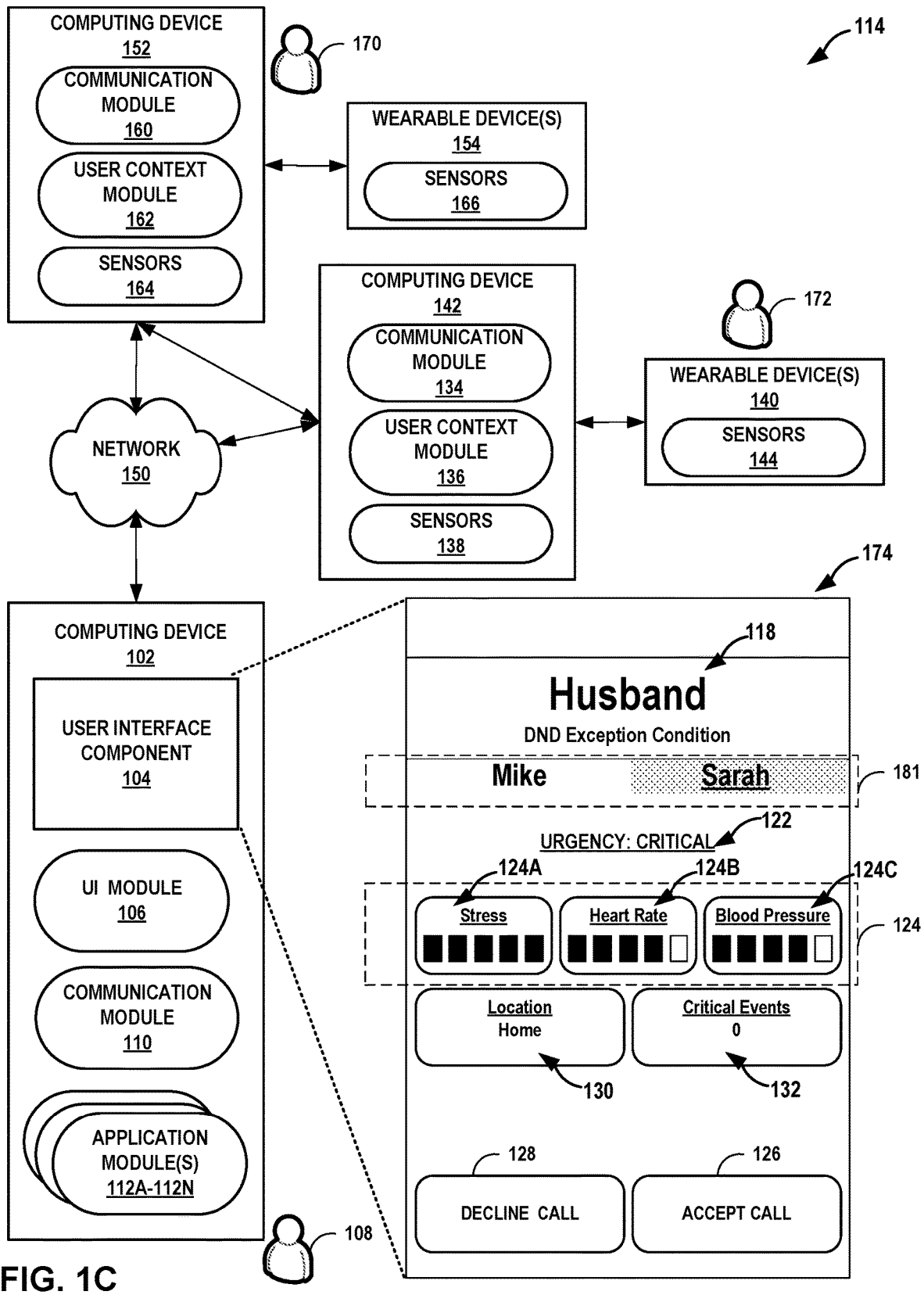

FIGS. 1A-1C are conceptual diagrams illustrating an example system 100 for providing health urgency context for communicating between computing devices, in accordance with one or more aspects of the present disclosure. In the example of FIG. 1A, system 100 includes computing device 102, computing device 152, health records system 180, network 150, and one or more wearable devices 154.

Computing devices 102 and 152 may each include, but is not limited to, portable or mobile devices such as mobile phones (including smart phones), laptop computers, tablet computers, wearable computing devices such as smart watches or computerized eyewear, smart television platforms, cameras, personal digital assistants (PDAs), etc. In some examples, computing devices 102 and 152 may include stationary computing devices such as desktop computers, servers, mainframes, etc.

Health records system 180 may represent any suitable remote computing system, such as one or more desktop computers, laptop computers, mainframes, servers, cloud computing systems, etc. capable of sending and receiving information across network 150. Health records system 180 may be a system that stores heath information, such as electronic medical records, associated with users, such as user 170. User 170 may be a user of computing device 152 or another person. Health records system 180 may communicate with computing devices 102 and 152 to receive health information associated with users of computing devices 102 and 152 and to send, to computing devices 102 and/or 152, health information, such as electronic medical records, associated with users, such as user 170.

Computing devices 102 and 152 may communicate via network 150. Network 150 may represent or include one or more public or private communication networks, such as a cellular network, Wi-Fi network, the Internet, and/or other types of networks for transmitting data between devices. Computing devices 102 and 152 and health records system 180 may send and receive data across network 150 using any suitable communication techniques. Network 150 may include network hubs, network switches, network routers, and other network devices that are operatively inter-coupled thereby providing for the exchange of information between computing devices 102 and 152 and health records system 180. Computing devices 102 and 152 and health records system 180 may be communicably coupled via one or more network links such as Ethernet, Asynchronous Transfer Mode (ATM) network, or other network connections, and such connections may be wireless and/or wired connections.

Computing device 152 may be communicatively coupled to one or more wearable computing devices 154. For instance, computing device 152 may use one or more communication protocols to send and receive data with one or more wearable computing devices 154. In some example examples, communication protocols may include Bluetooth®, Near-Field Communication, WiFi®, or any other suitable communication protocol. Examples of one or more wearable computing devices 154 may include a computerized watch, a computerized fitness band/tracker, computerized eyewear, computerized headwear, a computerized glove, etc. In some examples, wearable one or more wearable computing device 154 may include mobile computing device that can attach to and be worn on a person's body or clothing, such as attached to or worn on the body or clothing of user 170.

Computing device 152 and one or more wearable computing devices 154 may include sensors 164 and 166. In some examples, a sensor may be an input component that obtains environmental information of an environment that includes computing device 152 and/or one or more wearable computing devices 154. A sensor component may be an input component that obtains physiological information of a user (e.g., user 170) of computing device 152 and/or one or more wearable computing devices 154. In some examples, a sensor component may be an input component that obtains physical position, movement, and/or location information of computing device 152 and/or one or more wearable computing devices 154. For example, sensors 164 and 166 may include, but are not limited to: motion sensors (e.g., accelerometers, gyroscopes, etc.), physiological sensors that senses physiological information associated with user 170 (e.g., heart rate sensors, blood pressure sensors, stress sensors, blood oxygen saturation sensors, glucose sensors, electrodermal activity sensors, etc.), temperature sensors, position sensors, pressure sensors (e.g. a barometer), proximity sensors (e.g., an infrared sensor), ambient light detectors, location sensors (e.g., Global Positioning System sensor), or any other type of sensing component.

Computing device 152 also includes communication module 160 and user context 162. Modules 160 and 152 may perform operations described herein using software, hardware, firmware, or a mixture of both hardware, software, and firmware residing in and executing on computing device 152 or at one or more other remote computing devices. In some examples, modules 160 and 162 may be implemented as hardware, software, and/or a combination of hardware and software. Computing device 152 may execute modules 160 and 162 with one or more processors. Computing device 152 may execute any of modules 160 and 162 as or within a virtual machine executing on underlying hardware. Modules 160 and 162 may be implemented in various ways. For example, any of modules 160 and 162 may be implemented as a downloadable or pre-installed application or "app." In another example, any of modules 160 and 162 may be implemented as part of an operating system of computing device 152. Other examples of computing device 152 that implement techniques of this disclosure may include additional components not shown in FIG. 1A.

Communication module 160 of computing device 152 executes at computing device 152 to provide communication functionality for computing device 152 over, e.g., network 150. Such communication functionality may include sending and receiving voice calls, such as plain old telephone service (POTS) calls, voice over Internet Protocol (VoIP) calls, and the like. Such communication functionality may also include video calls, text messaging, multimedia messaging, and the like. Examples of communication module 160 may include a phone application, a video calling application, a voice calling application, a text messaging application, an instant messaging application, a video conferencing application, a social networking application, etc.

User context module 162 of computing device 152 executes at computing device 152 to determine, based on information determined by computing device 152 and/or one or more wearable devices 154, contextual information associated with the user of user context module 162, such as user 170 and the surroundings of user 170. User context module 162 may collect health parameters of user 170, such as based on data sensed by sensors 164 and 166 of computing device 152 and one or more wearable devices 154, such as the heart rate of user 170, the blood pressure of user 170, the oxygen saturation (SpO2) level of user 170, the stress level (e.g., electrodermal activity level) of user 170, the blood glucose level of user 170, and the like.

User context module 162 may also determine, based on data sensed by sensors 164 and 166 of computing device 152 and one or more wearable devices 154, the activity performed by user 170. For example, user context module 162 may determine, based on motion data and/or other information (e.g., heart rate information or other physiological information) sensed by motion sensors of sensors 164 and 166, the activity being performed by user 170. User context module 162 may also determine, based on data sensed by one or more location sensors of sensors 164 and 166 of computing device 152 and one or more wearable devices 154, the location of user 170. For example, if sensors 164 and 166 include a location sensor, such as a Global Positioning System (GPS) sensor, user context module 162 may receive GPS information from the GPS sensor.

User context module 162 may also determine and/or collect additional contextual information associated with user 170 and/or the surroundings of user 170. Such additional contextual information may include information regarding whether user 170 attended or missed previous medical appointments, a history of whether user 170 took and/or did not take medication at scheduled times, a history of whether user 170 picked up/did not pick up their prescription or other medication, the number of calls (e.g., voice calls, video calls, etc.) previously made by user 170, the weather at where user 170 is situated, and the like.

As shown in FIG. 1A, computing device 102 includes user interface component 104 ("UIC 104"), user interface module 106 ("UI module 106"), communication module 110, and application modules 112A-112N ("applications 112"). Modules 106, 110, and 112 may perform operations described herein using software, hardware, firmware, or a mixture of both hardware, software, and firmware residing in and executing on computing device 102 or at one or more other remote computing devices. In some examples, modules 106, 110, and 112 may be implemented as hardware, software, and/or a combination of hardware and software. Computing device 102 may execute modules 106, 110, and 112 with one or more processors. Computing device 102 may execute any of modules 106, 110, and 112 as or within a virtual machine executing on underlying hardware. Modules 106, 110, and 112 may be implemented in various ways. For example, any of modules 106, 110, and 112 may be implemented as a downloadable or pre-installed application or "app." In another example, any of modules 106, 110, and 112 may be implemented as part of an operating system of computing device 102. Other examples of computing device 102 that implement techniques of this disclosure may include additional components not shown in FIG. 1A.

Communication module 110 of computing device 102 may execute at computing device 102 to provide communication functionality for computing device 102 over, e.g., network 150. Such communication functionality may include sending and receiving voice calls, such as plain old telephone service (POTS) calls, voice over Internet Protocol (VoIP) calls, and the like. Such communication functionality may also include video calls, text messaging, multimedia messaging, and the like. Examples of communication module 110 may include a phone application, a video calling application, a voice calling application, a text messaging application, an instant messaging application, a video conferencing application, a social networking application, etc.

Communication module 110 may provide a do not disturb (DND) feature for computing device 102. While the do not disturb feature of computing device 102 is active, communication module 110 may silence calls, alerts, and/or notifications by muting audio alerts, stopping haptic output (e.g., vibrations), and/or blocking visual disturbances from being outputted by computing device 102 during certain situations. That is, communication module 110 may, in response to receiving a request to establish a communication session, such as when communication module 110 receives a voice call or a video call, communication module 110 may cause computing device 102 to refrain from outputting an audible alert (e.g., a ringtone) and/or to refrain from outputting haptic output (e.g., vibrations or other forms of haptic output) in response to receiving the request to establish a communication session, or may cause computing device 102 and/or other computing devices communicably coupled to computing device 102 (e.g., smart home systems, wearable devices, smart televisions, etc.) to provide any suitable form of output indicative of the request to establish the communication session.

In some examples, communication module 110 may determine one or more do not disturb exceptions that may be met by a request to establish a communication session received by communication module 110. A do not disturb exception is an exception to the do not disturb feature, such that while the do not turn feature is active, the do not disturb exception enables computing device 102 to output an audible alert, haptic output, or any other suitable forms of output in response to receiving a request to establish a communication session.

While the do not disturb feature of computing device 102 is active, communication module 110 may, in response to receiving a request to establish a communication session, determine whether the request to establish a communication session meets a do not disturb exception. If communication module 110 determines that the request to establish the communication session meets a do not disturb exception, communication module 110 may enable the request to establish the communication session to bypass the do not disturb feature and to enable computing device 102 to output an audible alert or haptic output in response to receiving a request to establish a communication session to indicate the request. For example, when computing device 102 receives a call, the do not disturb exception may cause computing device 102 to play a ringtone or to provide haptic output to alert the user of computing device 102 to the call.

In some examples, a do not disturb exception corresponds to an urgency level of a communication session. Specifically, a do not disturb exception may be associated with an urgency level threshold, and a request to establish the communication session may meet the do not disturb exception if the urgency level of the communication session meets or exceeds (i.e., is greater than or equal to) the urgency level threshold. In the example where the urgency level of a communication session ranges from one to five, communication module 110 may determine that a do not disturb exception associated with an urgency level threshold of three, so that requests to establish communication sessions associated with urgency levels of three or higher may meet the do not disturb exception for communication module 110.

UIC 104 of computing device 102 may function as an input device for computing device 102 and as an output device. For instance, UIC 104 may function as an input device using a resistive touchscreen, a surface acoustic wave touchscreen, a capacitive touchscreen, a projective capacitance touchscreen, a pressure sensitive screen, an acoustic pulse recognition touchscreen, or another presence-sensitive screen technology. UIC 104 may function as an output device using any one or more of a liquid crystal display (LCD), dot matrix display, light emitting diode (LED) display, microLED, organic light-emitting diode (OLED) display, e-ink, or similar monochrome or color display capable of outputting visible information to the user of computing device 102.

UIC 104 of computing device 102 may include a presence-sensitive screen that may receive tactile user input from a user of computing device 102. UIC 104 may receive the tactile user input by detecting one or more taps and/or gestures from a user of computing device 102 (e.g., the user touching or pointing to one or more locations of UIC 104 with a finger or a stylus pen). The presence-sensitive screen of UIC 104 may present output to a user. UIC 104 may present the output as a user interface, which may be related to functionality provided by computing device 102. For example, UIC 104 may present various functions and applications executing on computing device 102 such as an electronic message application, a messaging application, a map application, etc.

Application modules 112 may include functionality to perform any variety of operations on computing device 102. For instance, application modules 112 may include an email application, text messaging application, instant messaging application, weather application, video conferencing application, social networking application, weather application, stock market application, emergency alert application, sports application, office productivity application, multimedia player, etc. Although shown as operable by computing device 102, one or more of application modules 112 may be operable by a remote computing device that is communicatively coupled to computing device 102. In such examples, an application module executing at a remote computing device may cause the remote computing device to send the content and intent information using any suitable form of data communication (e.g., wired or wireless network, short-range wireless communication such as Near Field Communication or Bluetooth, etc.). In some examples, a remote computing device may be a computing device that is separate from computing device 102. For instance, the remote computing device may be operatively coupled to computing device 102 by a network. Examples of a remote computing device may include, but is not limited to a server, smartphone, tablet computing device, smart watch, and desktop computer. In some examples, a remote computing device may not be an integrated component of computing device 102.

UI module 106 may be implemented in various ways. For example, UI module 106 may be implemented as a downloadable or pre-installed application or "app." In another example, UI module 106 may be implemented as part of a hardware unit of computing device 102. In another example, UI module 106 may be implemented as part of an operating system of computing device 102. In some instances, portions of the functionality of UI module 106 or any other module described in this disclosure may be implemented across any combination of an application, hardware unit, and operating system.

UI module 106 may interpret inputs detected at UIC 104 (e.g., as a user provides one or more gestures at a location of UIC 104 at which user interface 14A or another example user interface is displayed). UI module 106 may relay information about the inputs detected at UIC 104 to one or more associated platforms, operating systems, applications, and/or services executing at computing device 102 to cause computing device 102 to perform a function. UI module 106 may also receive information and instructions from one or more associated platforms, operating systems, applications, and/or services executing at computing device 102 (e.g., application modules 112) for generating a GUI. In addition, UI module 106 may act as an intermediary between the one or more associated platforms, operating systems, applications, and/or services executing at computing device 102 and various output devices of computing device 102 (e.g., speakers, LED indicators, vibrators, etc.) to produce output (e.g., graphical, audible, tactile, etc.) with computing device 102.

In the example of FIG. 1A, one of application modules 112 and/or communication module 110 may send data to UI module 106 that causes UIC 104 to generate user interface 114 and elements thereof. In response, UI module 106 may output instructions and information to UIC 104 that cause UIC 104 to display a user interface of user interface 114 according to the information received from application modules 112 and/or communication module 110. When handling input detected by UIC 104, UI module 106 may receive information from UIC 104 in response to inputs detected at locations of a screen of UIC 104 at which elements of user interface 114 are displayed. UI module 106 disseminates information about inputs detected by UIC 104 to other components of computing device 102 for interpreting the inputs and for causing computing device 102 to perform one or more functions in response to the inputs.

In accordance with aspects of the present disclosure, user 170 may use communication module 160 of computing device 152 to send, to computing device 102, a request to establish a communication session with computing device 102, such as by placing a voice call, placing a video call, sending a text message, and the like to computing device 102. When computing device 152 sends a request to establish a communication session with computing device 102, computing device 152 may send certain contextual information indicative of an urgency level of the communication session to computing device 102.

The contextual information indicative of the urgency level of the communication session may be associated with the health of user 170 and may include health parameters of user 170, such as the heart rate of user 170, the blood pressure of user 170, the oxygen saturation (SpO2) level of user 170, the stress level (e.g., electrodermal activity level) of user 170, the blood glucose level of user 170, and the like. The contextual information may also include the activities currently or recently (e.g., in the last hour, in the last 12 hours, etc.) being performed by user 170, the location information associated with user 170, and the like.

User 170 of computing device 152 may interact with the settings of computing device 152 and/or communication module 160 to specify or otherwise customize the contextual information to be sent when computing device 152 establishes a communication session, so that user 170 may opt into or opt out of sending any piece of contextual information to another computing device. For example, user 170 may specify that different sets of contextual information be sent when establishing communication sessions with different computing devices, at different times of the day, on different days of the week, and the like. In some examples, communication module 160 may query user 170 regarding whether to send contextual information when computing device 152 establishes a communication session, and may require user 170 to explicitly authorize computing device 152 to send contextual information when computing device 152 establishes a communication session.

In some examples, the contextual information indicative of the urgency level of the communication session may indicate the urgency level of the communication session. When computing device 152 establishes a communication session with computing device 102, such as when communication module 160 initiates a voice call and/or a video call with computing device 102, communication module 160 may determine, based on the contextual information determined by user context module 162, an urgency level of the communication session, and may send an indication of the urgency level of the communication session to computing device 102.

Communication module 160 may determine the urgency level of the communication session based at least in part on the health parameters of user 170 and/or one or more critical events associated with user 170. A critical event associated with a user may be an event that indicates an increase in the likelihood that the user or a close family member of the user is suffering or will imminently suffer a health issue. Communication module 160 may determine one or more critical events associated with user 170 based on analyzing user 170's current and past events or locations.

For example, communication module 160 may determine an occurrence of a critical event associated with user 170 missing one or more medical appointments with a doctor or clinician. In another example, communication module 160 may determine an occurrence of a critical event associated with user 170 making a higher than normal number of calls (e.g., higher than a specified threshold of calls) in a past period of time, such as user 170 making more than 5 phone calls in the last 15 minutes to parties determined by computing device 152 to be close relatives of user 170. In another example, communication module 160 may determine an occurrence of a critical event associated with user 170 associated with a severe weather alert or a public emergency broadcast at user 170's location, such as a severe weather alert indicating a hurricane within 10 miles of user 170's location. In another example, communication module 160 may determine an occurrence of a critical event associated with user 170 being at an unusual location, such as user 170 being at a hospital or clinic outside of a scheduled appointment, user 170 being at a police station, user 170 being more than 30 miles away from user 170's office during working hours on the weekdays, and the like. In another example, communication module 160 may determine an occurrence of a critical event associated with user 170 not taking their medication at specified times or user 170 not picking up their medication from the pharmacy.

Communication module 160 may therefore determine the urgency level of the communication session based at least in part on the health parameters of user 170 and/or one or more critical events associated with user 170. Communication module 160 may receive, from user context module 162, health parameters of user 170 over an immediately preceding period of time, such as the health parameters of user 170 over the previous one hour, the previous two hours, the past day, and the like to determine sudden spikes or sudden drops in the levels of the health parameters that deviate from the health parameters' normal levels (e.g., baseline levels).

Examples of such health parameters include the heart rate of user 170, the blood pressure of user 170, the oxygen saturation (SpO2) level of user 170, the stress level (e.g., electrodermal activity level) of user 170, the blood glucose level of user 170, and the like. Computing device 152 may have previously determined baseline levels for each of the health parameters, and may compare, for each health parameter, the level of the health parameter over the immediately preceding period of time with the baseline level for the health parameter to determine an urgency level of each of the health parameters. In some examples, computing device 152 may determine the baseline levels for the health parameters from health information associated with user 170 received from health records system 180.

Communications module 160 may determine the urgency level of a health parameter to be one of lowest, low, normal, high, and severe. In some examples, if the level of a health parameter over the immediately preceding period of time deviates from the baseline level of the health parameter by less than or equal to 2%, then communication module 160 may determine the urgency level of the health parameter to be lowest. In some examples, if the level of a health parameter over the immediately preceding period of time deviates from the baseline level of the health parameter by between 2% and 5%, then communication module 160 may determine the urgency level of the health parameter to be low. In some examples, if the level of a health parameter over the immediately preceding period of time deviates from the baseline level of the health parameter by between 5% and 10%, then communication module 160 may determine the urgency level of the health parameter to be normal. In some examples, if the level of a health parameter over the immediately preceding period of time deviates from the baseline level of the health parameter by between 10% and 15%, then communication module 160 may determine the urgency level of the health parameter to be high. In some examples, if the level of a health parameter over the immediately preceding period of time deviates from the baseline level of the health parameter by over 15% then communication module 160 may determine the urgency level of the health parameter to be severe.

Communication module 160 may therefore determine the urgency level of the communication session based at least in part on the urgency level of each of the health parameters of user 170 and/or one or more critical events associated with user 170. In some examples, the urgency level of the communication session may range from one to five, where one is associated with the lowest amount of urgency and five is associated with the highest amount of urgency.

Communication module 160 may determine the urgency level of the communication session using any suitable algorithm or technique based on the urgency level of each of the health parameters of user 170 and/or one or more critical events associated with user 170. For example, communication module 160 may use a machine trained neural network algorithm to determine the urgency level of the communication session using the urgency level of each of the health parameters of user 170 and/or one or more critical events associated with user 170 as inputs into the algorithm.

In some examples, communication module 160 may determine an urgency level of the communication session is equal to 1 (i.e., the lowest level of urgency) if there are no critical events associated with user 170 and if the urgency level of each of the health parameters is normal, low, or lowest. In some examples, communication module 160 may determine an urgency level of the communication session is equal to 5 (i.e., the highest level of urgency) if at least one critical event is associated with user 170 or if the urgency level of at least one health parameter is severe.

Communication module 160 may therefore send a request to establish a communication session along with contextual information associated with the health of user 170 that is indicative of the urgency level of a communication session to computing device 102. The context information indicative of the urgency level of the communication session may include the urgency level of the communication session, the corresponding urgency levels of the health parameters of user 170, indications of one or more critical events associated with user 170, the location of user 170, the activity being performed by user 170, and the like.

In some examples, communication module 160 may send such data via network 150 using any suitable communications technique, such as Rich Communication Services (RCS). In some examples, communication module 160 may also send health information associated with user 170 received from health records system 180, such as the electronic medical records of user 170, to computing device 102. In some examples, communication module 160 may securely send contextual information associated with the health of user 170 in a secure fashion via encryption. For example, communication module 160 may encrypt the contextual information using an encryption key associated with computing device 102, such as a public encryption key associated with computing device 102.

In accordance with aspects of the present disclosure, communication module 110 of computing device 102 may receive, from computing device 152 via network 150, a request to establish a communication session with computing device 102. The request to establish a communication session may indicate an identity of the initiator of the communication session (e.g., the calling party of a voice call or video call), such as a phone number associated with computing device 152, an e-mail address associated with computing device 152, the name of user 170 using computing device 152, and the like. Communication module 110 may also receive, along with the request, contextual information indicative of the urgency level of a communication session. The context information indicative of the urgency level of the communication session may be associated with the health of user 170 and may include information such as the urgency level of the communication session, the corresponding urgency levels of the health parameters of user 170 of computing device 152, indications of one or more critical events associated with user 170, the location of user 170, the activity being performed by user 170, and the like.

In some examples, computing device 102 may, in response receiving the request to establish the communication session, output, along with an indication of the request to establish the communication session, such as an audible alert and/or haptic output, also output an indication of the request to establish the communication session at a display device. For example, computing device 102 may output user interface 114 that includes contextual information indicative of the urgency level of the communication session, such as one or more of: the urgency level of the communication session, the corresponding urgency levels of the health parameters of user 170 of computing device 152, indications of one or more critical events associated with user 170, the location of user 170, the activity being performed by user 170, and the like. In these examples, computing device 102 may, regardless of whether a do not disturb feature of computing device 102 is active at computing device 102, output such contextual information indicative of the urgency level of the communication session in response to receiving the request to establish the communication session.

In some examples, whether computing device 102 may, in response to receiving the request to establish the communication session, output contextual information indicative of the urgency level of the communication session may depend on whether the do not disturb feature of computing device 102 is active at computing device 102. If the do not disturb feature of computing device 102 is not active at computing device 102 when communication module 110 receives the request to establish the communication session, computing device 102 may, in response to receiving the request to establish the communication session, output an audible alert and/or haptic output indicative of the request to establish the communication session. Computing device 102 may also output an indication of the request to establish the communication session at a display device, such as by outputting user interface 114 that indicates the urgency level of the communication session. Computing device 102 may also output, such as in user interface 114, indications of the health parameters associated with user 170, the corresponding urgency levels of the health parameters, and/or other pieces of the contextual information received from computing device 152.

In some examples, computing device 102 may, in response to receiving the request to establish the communication session, also communicate with health records system 180 to receive health information associated with user 170 stored on health records system 180. Computing device 102 may therefore also output, such as in user interface 114, indications of the health parameters associated with user 170 received from health records system 180.

When the do not disturb feature of computing device 102 is active at computing device 102, communication module 110 may, in response to receiving a request to establish a communication session with computing device 152, determine whether the request to establish the communication session meets a do not disturb exception to determine whether to bypass the do not disturb feature. Communication module 110 may determine whether the request to establish the communication session meets a do not disturb exception based on contextual information indicative of the urgency level of the communication session, such as the urgency level of the communication session, the corresponding urgency levels of health parameters of user 170, the values of the health parameters of user 170, and the like. If computing device 102 determines that the request to establish the communication session meets a do not disturb exception, computing device 102 may enable the request to establish the communication level to bypass the do not disturb exception.

For example, if the request to establish a communication session indicates an urgency level of the communication session, communications module 110 may compare the urgency level of the communication session with an urgency level threshold associated with a do not disturb exception to determine if the request to establish the communication session meets the do not disturb exception. In some examples, if the urgency level of the communication session is greater than or equal to the urgency level threshold, communication module 110 may enable the request to establish the communication session to bypass the do not disturb feature. In other examples, if the urgency level of the communication session is greater than the urgency level threshold, communication module 110 may enable the request to establish the communication session to bypass the do not disturb feature.

In the example of FIG. 1A, the urgency levels of communication sessions may range from one to five. When the do not disturb feature of computing device 102 is active, a do not disturb exception of computing device 102 may be associated with an urgency level threshold of three, so that computing device 102 may determine that a request to establish a communication session received by computing device 102 may bypass the do not disturb feature of computing device 102 if the urgency level of a communication session is greater than or equal to the urgency level threshold of three. For example, if computing device 152 sends, to computing device 102, a request to establish a communication session that indicates an urgency level of five associated with the communication session, communication module 110 of computing device 102 may determine that the urgency level of the communication session is greater than the urgency level threshold and that the request to establish the communication session meets the do not disturb threshold associated with an urgency level threshold.

If communication module 110 determines that the request to establish the communication session may not bypass the do not disturb feature because the request does not meet a do not disturb exception, communication module 110 may log the request to establish the communication session at computing device 102, such as in a missed call log. In some examples, communication module 110 may log information associated with the request, such as the urgency level of the communication session, health parameters of user 170, corresponding urgency levels of the health parameters, and the like.

Communication module 110 may, in response to determining that the request to establish the communication session may bypass the do not disturb feature, enable the request to establish the communication session to bypass the do not disturb feature of computing device 102. Enabling the request to bypass the do not disturb feature of computing device 102 may cause computing device 102 to play a ringtone or to provide haptic output to alert the user of computing device 102 to communication module 110 receiving the request to establish the communication session.

Enabling the request to bypass the do not disturb feature of computing device 102 or if the do not disturb feature of computing device 102 is not active may cause communication module 110 to, in response to receiving the request to establish the communication session, send data to UI module 106 that causes UIC 104 to output user interface 114 associated with the request to establish the communication session between computing device 102 and computing device 152 so that a user of computing device 102 may provide user input at UIC 104 to accept or decline the request. In the example where the request to establish the communication session is a call from computing device 152, such as a voice call or an audio call, enabling the request to bypass the do not disturb feature of computing device 102 may also cause communication module 110 to send data to UI module 106 that causes UIC 104 to generate user interface 114 that is an incoming call user interface with which a user of computing device 102 may interact by providing input at UIC 104 with to accept the call or to decline the call.

As shown in FIG. 1A, UI module 106 may cause UIC 104 to output, in user interface 114, information associated with the request to establish communications, such as UI element 118 that indicates an identity of the initiator of the communication session (e.g., the calling party of a voice call or video call), such as a phone number associated with computing device 152, an e-mail address associated with computing device 152, the name of user 170 using computing device 152, and the like. UI module 106 may also cause UIC 104 to output, in user interface 114, UI element 122 that indicates the urgency level of the communication session.

UI module 106 may also cause UIC 104 to output, in user interface 114, UI elements 124 that indicate the health parameters of user 170 of computing device 152, such as UI element 124A that indicates the stress level of user 170 UI element 124B that indicates the heart rate of user 170, and UI element 124C that indicates the blood pressure of user 170. UI module 106 may also cause UIC 104 to output, in user interface 114, UI element 130 that indicates the location of user 170 and UI element 132 that indicates the number of critical events associated with user 170.

In addition, UI module 106 may cause UIC 104 to output, in user interface 114, UI controls 126 and 128 with which the user of computing device 102 may interact to accept the request to establish the communication session with computing device 152 or to decline the request to establish the communication session with computing device 152. In the example where the request to establish the communication session with computing device 152 is a request to accept a call, UI control 126 may be an accept call button that the user may select via UIC 104 to accept the call and UI control 128 may be a decline call button that the user may select via UIC 104 to decline the call. The user of computing device 102 may therefore interact with UI control 126 or UI control 128 to accept or decline the request to establish the communication session with computing device 152. Communication module 110 may, in response to the user interacting via UI component 104 to select UI control 126 to accept the request to establish the communication session with computing device 152, establish the requested communication session with computing device 152, such as by connecting a video call or voice call from computing device 152 with computing device 102 via network 150.

In some examples, a computing device may send a request to establish a communication session along with context information associated with a third-party user (e.g., a user other than the user of the computing device). The contextual information may indicate the urgency level of the communication session based on information such as the health parameters of the third-party user, one or more critical events associated with the third-party user, the location of the third-party user, the activity being performed by the third-party user, and the like. That is, a user, when placing a call, may share the health information as well as other contextual information of a third-party user, so that the recipient of the call may receive information regarding the third-party user that is not a party to the call. Further, the urgency level of the call may also be based on the contextual information associated with the third-party user.

In some examples, a group of people (i.e., users) that are known to each other may explicitly give each other permission share their contextual information, such as health information, to other people in the same group when using their computing devices to send requests to establish communication sessions with other computing devices. These groups of people may, for example, be members of the same family. Thus, for example, a husband may be able to share his daughter's health information when the husband makes a call to his wife, and the husband may, as part of the call communicate an urgency level of the call that is based on the daughter's health information.

As shown in FIG. 1B, user 108 of computing device 102, user 170 of computing device 152, and user 172 of computing device 142 may be members of a group that have explicitly give each other permission share their health information as well as other contextual information to other users in the same group. For example, user 170 may be the husband of user 108 and the father of user 172. User 108 may be the wife of user 170 and may be the mother of user 172. User 172 may be the daughter of users 108 and 170. As such, computing devices 102, 152, and 142 may share health information of any of users 108, 170, and 172 with each other, such as when sending requests to establish communication sessions with each other.

As described in FIG. 1A, computing device 152 may determine contextual information of user 170 via use of wearable device 154, sensors 164 and 166, and user context module 162. Computing device 142 may be similar to computing device 152 and may determine contextual information of user 172 via use of wearable device 140, sensors 138 and 144, and user context module 136. Wearable device 140 may be similar to wearable device 154, sensors 138 and 144 may be similar to sensors 164 and 166. User context module 136 may be similar to user context module 162. Communication module 134 may be similar to communication module 160.

For example, user context module 136 may execute at computing device 142 to determine, based on information determined by computing device 142 and/or one or more wearable devices 140, contextual information associated with the user of user context module 136, such as user 172 and the surroundings of user 172. User context module 136 may collect health parameters of user 172, such as based on data sensed by sensors 138 and 144, such as the heart rate of user 172, the blood pressure of user 172, the oxygen saturation (SpO2) level of user 172, the stress level (e.g., electrodermal activity level) of user 172, the blood glucose level of user 170, and the 172.

User context module 136 may also determine, based on data sensed by sensors 138 and 144, the activity performed by user 172. For example, user context module 136 may determine, based on motion data and/or other information (e.g., heart rate information or other physiological information) sensed by motion sensors of sensors 138 and 144, the activity being performed by user 172. User context module 136 may also determine, based on data sensed by one or more location sensors of sensors 138 and 144, the location of user 172.

User context module 136 may also determine and/or collect additional contextual information associated with user 172 and/or the surroundings of user 172. Such additional contextual information may include information regarding whether user 172 attended or missed previous medical appointments, a history of whether user 172 took and/or did not take medication at scheduled times, a history of whether user 172 picked up/did not pick up their prescription or other medication, the number of calls (e.g., voice calls, video calls, etc.) previously made by user 172, the weather at where user 172 is situated, and the like.

In some examples, computing device 142 may determine an urgency level of the communication session based on the contextual information associated with user 172 based on techniques similar to that used by computing device 152 to determine an urgency level of the communication session based on the contextual information associated with user 172. For example, computing device 142 may determine an urgency level of the communication session based on corresponding urgency levels of the health parameters of user 172, whether the contextual information associated with user 172 is indicative of one or more critical events, and the like.

In some examples, the contextual information associated with users 108, 170, and 172 collected by computing devices 102, 152, and 142 may be collected and stored in a central location, such as on the cloud, via network 150. Each of computing devices 102, 152, and 142 may continuously collect and/or determine the contextual information associated with users 108, 170, and 172 and may store such information at a central location, and each of computing devices 102, 152, and 142 may be able to access information collected and stored by computing devices 102, 152, and 142 at the central location.

In other examples, computing devices in the same group may directly exchange the collected contextual information. In the example of FIG. 1B, computing devices 102, 152, and 142 are used by users 108, 170, and 172 in a group of users that have explicitly given each other permission share their contextual information, such as health information, to other users in the same group. When computing devices 152 and 142 are within a specified range of each other, such as within 100 meters, within 50 meters, within range of Bluetooth communications, and the like, computing devices 152 and 142 may communicate with each other directly via short-range communications, such as Bluetooth, to exchange contextual information associated with users 170 and 172, or may exchange contextual information associated with users 170 and 172 via network 150, such as by retrieving contextual information associated with users 170 and 172 stored in the cloud.

User 170 may therefore use computing device 152 to send a request to establish a communication session to computing device 102 used by user 108 along with contextual information associated with user 170 of computing device 152. In some examples, computing device 152 may, in response to user 170 providing user input at computing device 152 to send the request, such as when user 170 uses the phone application on computing device 152 to place a call to user 108, determine whether any computing devices being used by any other users in a group with user 170 and user 108 are proximate (e.g., within a specified distance from) to user 170 and, if so, may request and receive contextual information associated with the users of such computing devices. For example, computing device 152 may determine that computing device 142 being used by user 172 that is part of the group with user 170 and user 108 is proximate to computing device 152 and may, in response, prompt user 170 as to whether to also send contextual information associated with user 172 to computing device 102 along with the request to establish the communication session. If user 170 provides user input at computing device 152 to direct computing device 152 to send contextual information associated with user 172 to computing device 102 along with the request to establish the communication session, computing device 152 may retrieve the latest contextual information associated with user 172, either directly from computing device 142 or via a third-party server, such as from the cloud.

In some examples, computing device 152 may receive contextual information associated with users of computing devices even when such users are not proximate to computing device 152. For example, computing device 152 may prompt user 170 as to whether to also send contextual information associated with user 172 to computing device 102 along with the request to establish the communication session regardless of whether user 172 is proximate to computing device 152. If user 170 provides user input at computing device 152 to direct computing device 152 to send contextual information associated with user 172 to computing device 102 along with the request to establish the communication session, computing device 152 may retrieve the latest contextual information associated with user 172, either directly from computing device 142 or via a third-party server, such as from the cloud.

In some examples, computing device 152 may receive contextual information associated with users of computing devices that are part of the same group as user 170, where the group of users have explicitly allowed their contextual information to be shared, but may prompt user 170 as to whether to also send contextual information associated with these other users only if the urgency level of the users are at or above an urgency threshold. For example, computing device 152 may, in response to user 170 providing user input at computing device 152 to send the request, such as when user 170 uses the phone application on computing device 152 to place a call to user 108, determine whether any other users in a group with user 170 and user 108 are associated with an urgency level of the communication session that meets or exceeds an urgency threshold. If computing device 152 determines that, for example, the urgency level of user 172 is at or above the urgency threshold, computing device 152 may send contextual information associated with user 172 to computing device 102 along with the request to establish the communication session.

As such, when computing device 152 is proximate to computing device 142, computing device 152 may, when sending a request to establish a communication session with computing device 102, also send, to computing device 102, contextual information associated with user 170 of computing device 152 as well as contextual information associated with user 172.

Communication module 160 may determine, for the request to establish the communication session, contextual information indicative of the urgency level of the communication session. For example, communication module 160 may determine both contextual information indicative of an urgency level of the communication session that is associated with the health of user 170 as well as contextual information indicative of an urgency level of the communication session that is associated with the health of user 172.

Similar to the techniques described in FIG. 1A, contextual information indicative of an urgency level of the communication session that is associated with the health of user 170 may include health parameters of the user, the activities currently or recently (e.g., in the last hour, in the last 12 hours, etc.) being performed by user 170, the location information associated with user 170, and the like. The urgency level of the communication session may also be an urgency level determined based at least in part on the health parameters of user 170 and/or one or more critical events associated with user 170. Communication module 160 may determine one or more critical events associated with user 170 based on analyzing user 170's current and past events or locations.

Similarly, contextual information indicative of an urgency level of the communication session that is associated with the health of user 172 may include health parameters of the user, the activities currently or recently (e.g., in the last hour, in the last 12 hours, etc.) being performed by user 172, the location information associated with user 172, and the like. The urgency level of the communication session may also be an urgency level determined based at least in part on the health parameters of user 172 and/or one or more critical events associated with user 172. Communication module 160 may determine one or more critical events associated with user 172 based on analyzing user 172's current and past events or locations.

Communication module 160 may therefore send a request to establish a communication session along with contextual information associated with the health of user 170 that is indicative of the urgency level of a communication session to computing device 102. The context information indicative of the urgency level of the communication session may include the urgency level of the communication session, the corresponding urgency levels of the health parameters of user 170, indications of one or more critical events associated with user 170, the location of user 170, the activity being performed by user 170, and the like. Similarly, communication module 160 may also send contextual information associated with the health of user 172 that is indicative of the urgency level of a communication session to computing device 102. The context information indicative of the urgency level of the communication session may include the urgency level of the communication session, the corresponding urgency levels of the health parameters of user 172, indications of one or more critical events associated with user 172, the location of user 172, the activity being performed by user 172, and the like. As can be seen, the communication module 160 may send indications of both an urgency level of the communication session based on contextual information associated with user 170 as well as an urgency level of the communication based on contextual information associated with user 172.

Communication module 110 of computing device 102 may receive, from computing device 152 via network 150, a request to establish a communication session with computing device 102. The request to establish a communication session may indicate an identity of the initiator of the communication session (e.g., the calling party of a voice call or video call), such as a phone number associated with computing device 152, an e-mail address associated with computing device 152, the name of user 170 using computing device 152, and the like. Communication module 110 may also receive, along with the request, contextual information indicative of the urgency level of a communication session. The context information indicative of the urgency level of the communication session may indicate both an urgency level of the communication session based on contextual information associated with user 170 as well as an urgency level of the communication session based on contextual information associated with user 172. For example, the contextual information may include information such as the urgency level of user 170, the corresponding urgency levels of the health parameters of user 170, indications of one or more critical events associated with user 170, the location of user 170, the activity being performed by user 170, and the like. The contextual information may also include information such as the urgency level of user 172, the corresponding urgency levels of the health parameters of user 172, indications of one or more critical events associated with user 172, the location of user 172, the activity being performed by user 172, and the like.

If the do not disturb feature of computing device 102 is not active at computing device 102 when communication module 110 receives the request to establish the communication session, computing device 102 may, in response to receiving the request to establish the communication session, output an audible alert and/or haptic output indicative of the request to establish the communication session. Computing device 102 may also output an indication of the request to establish the communication session at a display device, such as by outputting user interface 114 that indicates the urgency level of the communication session. Computing device 102 may also output, such as in user interface 174, indications of the health parameters associated with user 170, the corresponding urgency levels of the health parameters of user 170, and/or other pieces of the contextual information associated with user 170. In some examples, computing device 102 may also output, in user interface 174, indications of the health parameters associated with user 172, the corresponding urgency levels of the health parameters of user 172, and/or other pieces of the contextual information associated with user 172.

When the do not disturb feature of computing device 102 is active at computing device 102, communication module 110 may, in response to receiving a request to establish a communication session with computing device 152, determine whether the request to establish the communication session meets a do not disturb exception to determine whether to bypass the do not disturb feature. Communication module 110 may determine whether the request to establish the communication session meets a do not disturb exception based on contextual information indicative of the urgency level of the communication session, such as the urgency level of the communication session associated with user 170, the corresponding urgency levels of health parameters of user 170, the values of the health parameters of user 170, the urgency level of the communication session associated with user 172, the corresponding urgency levels of health parameters of user 172, the values of the health parameters of user 172, and the like. If computing device 102 determines that the request to establish the communication session meets a do not disturb exception, computing device 102 may enable the request to establish the communication level to bypass the do not disturb exception.

Communication module 110 may determine whether the request to establish the communication session meets a do not disturb exception based on both the contextual information associated with user 170 as well as the contextual information associated with user 172. That is, in some examples, only one of the contextual information associated with user 170 and the contextual information associated with user 172 may have to meet the do not disturb exception for communication module 110 to determine that the request to establish the communication session meets the do not disturb exception.

If communication module 110 determines that the request to establish the communication session may not bypass the do not disturb feature because the request does not meet a do not disturb exception, communication module 110 may log the request to establish the communication session at computing device 102, such as in a missed call log. In some examples, communication module 110 may log information associated with the request, such as the urgency level of the communication session associated with user 170, health parameters of user 170, corresponding urgency levels of the health parameters of user 170, the urgency level of the communication session associated with user 172, health parameters of user 172, corresponding urgency levels of the health parameters of user 172, and the like.

Communication module 110 may, in response to determining that the request to establish the communication session may bypass the do not disturb feature, enable the request to establish the communication session to bypass the do not disturb feature of computing device 102. Enabling the request to bypass the do not disturb feature of computing device 102 may cause computing device 102 to play a ringtone or to provide haptic output to alert the user of computing device 102 to communication module 110 receiving the request to establish the communication session.

Enabling the request to bypass the do not disturb feature of computing device 102 or if the do not disturb feature of computing device 102 is not active may cause communication module 110 to, in response to receiving the request to establish the communication session, send data to UI module 106 that causes UIC 104 to output user interface 174 associated with the request to establish the communication session between computing device 102 and computing device 152 so that a user of computing device 102 may provide user input at UIC 104 to accept or decline the request. In the example where the request to establish the communication session is a call from computing device 152, such as a voice call or an audio call, enabling the request to bypass the do not disturb feature of computing device 102 may also cause communication module 110 to send data to UI module 106 that causes UIC 104 to generate user interface 174 that is an incoming call user interface with which a user of computing device 102 may interact by providing input at UIC 104 with to accept the call or to decline the call.

As shown in FIG. 1B, UI module 106 may cause UIC 104 to output, in user interface 174, information associated with the request to establish communications, such as UI element 118 that indicates an identity of the initiator of the communication session (e.g., the calling party of a voice call or video call), such as a phone number associated with computing device 152, an e-mail address associated with computing device 152, the name of user 170 using computing device 152, and the like.

Module 106 may also cause UIC 104 to output, in user interface 174, contextual information associated with user 170 as well as contextual information associated with user 172. UI module 106 may cause UIC 104 to output UI element 181 that can be selected to toggle between outputting contextual information associated with user 170 and contextual information associated with user 172. For example, UI element 181 may include the name of user 170, which may be "Mike" and the name of user 170, which may be "Sarah." When "Mike" is selected, UI module 106 may cause UIC 104 to output, in user interface 174, contextual information associated with user 170.

For example, UI module 106 may also cause UIC 104 to output, in user interface 174, UI element 122 that indicates the urgency level of the communication session that is determined from the contextual information associated with user 170. UI module 106 may also cause UIC 104 to output, in user interface 174, UI elements 124 that indicate the health parameters of user 170 of computing device 152, such as UI element 124A that indicates the stress level of user 170 UI element 124B that indicates the heart rate of user 170, and UI element 124C that indicates the blood pressure of user 170. UI module 106 may also cause UIC 104 to output, in user interface 114, UI element 130 that indicates the location of user 170 and UI element 132 that indicates the number of critical events associated with user 170.

In addition, UI module 106 may cause UIC 104 to output, in user interface 174, UI controls 126 and 128 with which the user of computing device 102 may interact to accept the request to establish the communication session with computing device 152 or to decline the request to establish the communication session with computing device 152. In the example where the request to establish the communication session with computing device 152 is a request to accept a call, UI control 126 may be an accept call button that the user may select via UIC 104 to accept the call and UI control 128 may be a decline call button that the user may select via UIC 104 to decline the call. The user of computing device 102 may therefore interact with UI control 126 or UI control 128 to accept or decline the request to establish the communication session with computing device 152. Communication module 110 may, in response to the user interacting via UI component 104 to select UI control 126 to accept the request to establish the communication session with computing device 152, establish the requested communication session with computing device 152, such as by connecting a video call or voice call from computing device 152 with computing device 102 via network 150.

As shown in FIG. 1C, when "Sarah" is selected in UI element 181, which is the name of user 172, UI module 106 may cause UIC 104 to output, in user interface 174, contextual information associated with user 172.

For example, UI module 106 may also cause UIC 104 to output, in user interface 174, UI element 122 that indicates the urgency level of the communication session that is determined from the contextual information associated with user 172. UI module 106 may also cause UIC 104 to output, in user interface 174, UI elements 124 that indicate the health parameters of user 172 of computing device 152, such as UI element 124A that indicates the stress level of user 170 UI element 124B that indicates the heart rate of user 172, and UI element 124C that indicates the blood pressure of user 172. UI module 106 may also cause UIC 104 to output, in user interface 114, UI element 130 that indicates the location of user 172 and UI element 132 that indicates the number of critical events associated with user 172.

Figure 2:
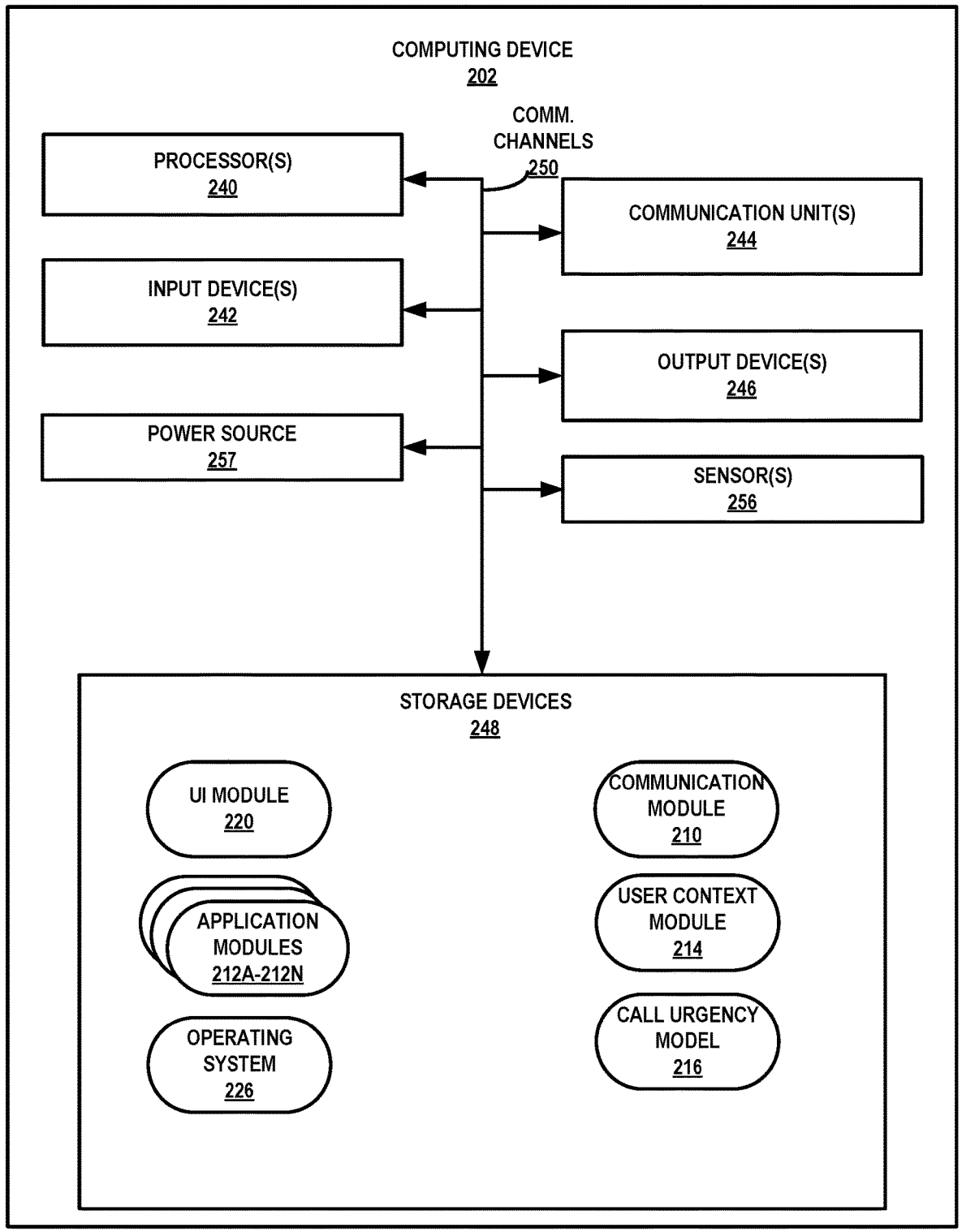
FIG. 2 is a block diagram illustrating an example computing device, in accordance with one or more aspects of the present disclosure.

FIG. 2 is a block diagram illustrating an example computing device, in accordance with one or more aspects of the present disclosure. The example computing device 202 illustrated in FIG. 2 may be an example of computing device 102 or computing device 152 of FIGS. 1A-1C. FIG. 2 illustrates only one particular example of computing device 202, and many other examples of computing device 202 may be used in other instances and may include a subset of the components included in example computing device 202 or may include additional components not shown in FIG. 2.

As shown in the example of FIG. 2, computing device 202 includes one or more processors 240, one or more input devices 242, one or more communication units 244, one or more output devices 246, one or more storage devices 248, and one or more sensors 256. One or more input devices 242 and one or more output devices 246 may be examples of UIC 104 of FIGS. 1A-1C. Storage devices 248 of computing device 202 also include UI module 220, application modules 212, operating system 226, communication module 210, user context module 214, and call urgency model 216. Communication channels 250 may interconnect each of the components 240, 242, 244, 246, 248, and 256 for inter-component communications (physically, communicatively, and/or operatively). In some examples, communication channels 250 may include a system bus, a network connection, one or more inter-process communication data structures, or any other components for communicating data between hardware and/or software.

One or more processors 240 may implement functionality and/or execute instructions within computing device 202. For example, processors 240 on computing device 202 may receive and execute instructions stored by storage devices 248 that provide the functionality of UI module 220, application modules 212, operating system 226, communication module 210, user context module 214, and call urgency model 216. These instructions executed by processors 240 may cause computing device 202 to store and/or modify information, within storage devices 248 during program execution. Processors 240 may execute instructions of UI module 220, application modules 212, operating system 226, communication module 210, user context module 214, and call urgency model 216 to perform one or more operations. That is, UI module 220, application modules 212, operating system 226, communication module 210, user context module 214, and call urgency model 216 may be operable by processors 240 to perform various functions described herein.

One or more input devices 242 and one or more output devices 245 of computing device 202 may be an example of UIC 104 of FIGS. 1A-1C. One or more input devices 242 of computing device 202 may receive input. Examples of input are tactile, audio, kinetic, and optical input, to name only a few examples. Input devices 242 of computing device 202, in one example, include a mouse, keyboard, voice responsive system, video camera, buttons, control pad, microphone or any other type of device for detecting input from a human or machine. In some examples, input device 42 may be a presence-sensitive input device, which may include a presence-sensitive screen, touch-sensitive screen, etc.

One or more output devices 246 of computing device 202 may generate output. Examples of output are tactile (e.g. haptic), audio, and video output. Output devices 246 of computing device 202, in one example, include a presence-sensitive screen, sound card, video graphics adapter card, one or more audio output devices such as speakers, a vibration motor (e.g., linear actuators) for outputting haptic output, cathode ray tube (CRT) monitor, liquid crystal display (LCD), or any other type of device for generating output to a human or machine. Output devices 246 may include display devices such as cathode ray tube (CRT) monitor, liquid crystal display (LCD), Light-Emitting Diode (LED) or any other type of device for generating tactile, audio, and/or visual output.

One or more communication units 244 of computing device 202 may communicate with external devices by transmitting and/or receiving data. For example, computing device 202 may use communication units 244 to transmit and/or receive radio signals on a radio network such as a cellular radio network. In some examples, communication units 244 may transmit and/or receive satellite signals on a satellite network such as a Global Positioning System (GPS) network. Examples of communication units 244 include a network interface card (e.g. such as an Ethernet card), an optical transceiver, a radio frequency transceiver, a GPS receiver, or any other type of device that can send and/or receive information. Other examples of communication units 244 may include Bluetooth®, GPS, 3G, 4G, and Wi-Fi® radios found in mobile devices as well as Universal Serial Bus (USB) controllers and the like.

One or more storage devices 248 within computing device 202 may store information for processing during operation of computing device 202. In some examples, storage devices 248 is a temporary memory, meaning that a primary purpose of storage devices 248 is not long-term storage. Storage devices 248 on computing device 202 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage devices 248, in some examples, also include one or more computer-readable storage media. Storage devices 248 may be configured to store larger amounts of information than volatile memory. Storage devices 248 may further be configured for long-term storage of information as non-volatile memory space and retain information after activate/off cycles. Examples of non-volatile memories include magnetic hard discs, optical discs, flash memories, or forms of electrically programmable memories (EPROM) or electrically erasable and programmable (EEPROM) memories. Storage devices 248 may store program instructions and/or data associated with UI module 220, application modules 212, operating system 226, communication module 210, user context module 214, and call urgency model 216. Application modules 212 may be similar to one or more application modules 112 of FIGS. 1A-1C. Operating system 226 may be an operating system that executes at computing device 202, such as a smart phone operating system. UI module 220 is similar to UI module 106 of FIGS. 1A-1C.

As shown in FIG. 2, computing device 202 may include one or more sensors 256. Sensors 256 may include one or more motion sensors, such as an accelerometer that generates accelerometer data and/or a gyrometer that generates gyrometer data. Accelerometer data may indicate an acceleration and/or a change in acceleration of computing device 202. Gyrometer data may indicate a physical orientation and/or change in physical orientation of computing device 202. In some examples, the orientation may be relative to one or more reference points. Sensors 256 may include a magnetometer that generates magnetometer data. Magnetometer data may indicate the magnetization of an object that is touching or in proximity to computing device 202. Magnetometer data may indicate the Earth's magnetic field, and in some examples, provide directional functionality of a compass. Sensors 256 may include an ambient light sensor that generates ambient light data. The ambient light data may indicate an intensity of light to which computing device 202 is exposed. Sensors 256 may include a proximity sensor that generates proximity data. Proximity data may indicate whether an object is within proximity to computing device 202. In some examples, proximity data may indicate how close an object is to computing device 202. In some examples, sensors 256 may include a clock that generates a date and time. The date and time may be a current date and time. In some examples, one or more sensors 256 may include a location sensor such as a GPS sensor or any other suitable sensors.

In some examples, one or more sensors 256 may include one or more physiological sensors that senses physiological information associated with the user of computing device 202. Examples of one or more physiological sensors may include a heart rate sensor, a blood pressure sensor, a stress sensor (e.g., an electrodermal activity sensor), a body temperature sensor, a glucose sensor, a blood oxygen saturation sensor, and the like. The physiological sensors of one or more sensors 256 may continuously monitor health parameters of the user of computing device 202, such as monitoring the heart rate, the blood pressure, the stress level, the body temperature, the blood glucose level, the oxygen saturation level, and the like of the user, and one or more processors 240 may store these health parameters of the user over time in one or more storage devices 248 as, for example, baseline data for each of the health parameters.

As shown in FIG. 2, computing device 202 may include a power source 257. In some examples, power source 257 may be a battery. Power source 257 may provide power to one or more components of computing device 202. Examples of power source 257 may include, but are not necessarily limited to, batteries having zinc-carbon, lead-acid, nickel cadmium (NiCd), nickel metal hydride (NiMH), lithium ion (Li-ion), and/or lithium ion polymer (Li-ion polymer) chemistries. In some examples, power source 257 may have a limited capacity (e.g., 1000-3000 mAh).

In accordance with techniques of the disclosure, computing device 202 may include one or more processors 240 that are configured to execute communication module 210 to perform communication functionality, such as sending and receiving voice calls, video calls, and the like. Specifically, communication module 210 may execute to establish communication sessions with remote computing devices via networks such as network 150 of FIGS. 1A-1C. For example, communication module 210 may be an example of a phone call application, a VoIP application, a video conferencing application, a video calling application, a text messaging application, a social media application, and the like.

A user of computing device 202 may interact with communication module 210 by providing user input at one or more input devices 242 to cause communication module 210 to send a request to establish a communication session with a remote computing device, such as by interacting with communication module 210 to call a phone number associated with the remote computing device, to start a video conferencing call with the remote computing device, and the like.

When the user of computing device 202 causes communication module 210 to send, to a remote device, a request to establish a communication session with the remote computing device, such as when the user interacts with communication module to place a call to the remote computing device, communication module 210 may communicate with user context module 214 to determine contextual information associated with the user of computing device 202. Communication module 210 may determine, based on the contextual information associated with the user of computing device 202, an urgency level of the communication session.

User context module 214 may execute at one or more processors 240 to determine contextual information associated with the user of computing device 202. In some examples, user context module 214 may determine contextual information associated with the user of computing device 202 based on sensor data provided by one or more sensors 256 of computing device 202. In some examples, user context module 214 may also receive, via one or more communication units 244, sensor data provided by one or more sensors of one or more wearable computing devices worn by or attached to the user of computing device 202, and may determine contextual information associated with the user of computing device 202 based on sensor data provided by one or more sensors 256 and/or one or more sensors of one or more wearable computing devices.

User context module 214 may determine contextual information associated with the user, such as health information associated with the user, the location of the user, an activity being performed or was recently performed by the user, and/or one or more critical events associated with the user. User context module 214 may determine the location of the user using location data provided by a location sensor, and may use the location data received from a location sensor to map the location of the user to a specific place, such as to the user's home, user's work office, a hospital or a clinic, a supermarket, a park, a police station, and the like. User context module 214 may perform activity recognition to determine the activity being performed by the user or recently performed by the user using sensor data provided by a motion sensor as well as one or more other sensors. Examples of the activity being performed by the user may include whether the user is working out or otherwise physically exerting themselves, whether the user is driving a vehicle or riding in a vehicle, whether the user is walking or running, and the like.

User context module 214 may determine, based at least in part on the sensor data, one or more critical events associated with the user. A critical event associated with the user may occur when user context module 214 determines that the user missed one or more medical appointments with a doctor or clinician, the user making a higher than normal number of calls (e.g., higher than a specified threshold of calls) in a past period of time, the occurrence of a severe weather alert or a public emergency broadcast at the location of the user, the user being at an unusual location, and/or the user not taking their medication at scheduled times/days or the user not picking up their medication from the pharmacy.

User context module 214 may determine, for each health parameter of the user, a corresponding urgency level of the health parameter. To determine the corresponding urgency level of a health parameter, user context module 214 may compare the health parameter collected over the immediately preceding period of time by one or more sensors with the baseline level for the health parameter. User context module 214 may determine deviations in the health parameter over the immediately preceding period of time from the baseline level, and may determine, based on such deviations, the corresponding urgency level of the health parameter.

In some examples, user context module 214 may determine the corresponding urgency level of a health parameter to be one of lowest, low, normal, high, and severe. In some examples, if the health parameter over the immediately preceding period of time deviates from the baseline level of the health parameter by less than or equal to 2%, then user context module 214 may determine the corresponding urgency level of the health parameter to be lowest. In some examples, if the health parameter over the immediately preceding period of time deviates from the baseline level of the health parameter by between 2% and 5%, then user context module 214 may determine the corresponding urgency level of the health parameter to be low. In some examples, if the health parameter over the immediately preceding period of time deviates from the baseline level of the health parameter by between 5% and 10%, then user context module 214 may determine the corresponding urgency level of the health parameter to be normal. In some examples, if the health parameter over the immediately preceding period of time deviates from the baseline level of the health parameter by between 10% and 15%, then user context module 214 may determine the corresponding urgency level of the health parameter to be high. In some examples, if the health parameter over the immediately preceding period of time deviates from the baseline level of the health parameter by over 15% then user context module 214 may determine the corresponding urgency level of the health parameter to be severe.

Communication module 210 may determine, based on the contextual information associated with the user of computing device 202, an urgency level of the communication session. Specifically, communication module 210 may determine, based on the contextual information such as the health parameters of the user, the corresponding urgency levels of the health parameters of the user, one or more critical events associated with the user, activity being performed or was recently performed by the user, the location of the user, etc. to determine the urgency level of the communication session.

In some examples, communication module 210 may use call urgency model 216 that executes at one or more processors 240 to determine, based on such contextual information associated with the user, the urgency level of a communication session. Call urgency model 216 may be a machine trained model that includes one or more neural networks. The one or more neural networks may include multiple interconnected nodes, and each node may apply one or more functions to a set of input values that correspond to one or more features, and provide one or more corresponding output values. The one or more features may be contextual information associated with the user, and the one or more corresponding output values of one or more neural networks may be an indication of the urgency level of a communication session.

The one or more corresponding output values may, in some examples, include probabilities of the urgency level of the communication session. Accordingly, call urgency model 216 may use one or more neural networks to determine probabilities of the urgency level of the communication session based on the features of the user input, and may determine and output an indication of the urgency level having the highest probability of being the urgency level of a communication session based on the corresponding probabilities.

Call urgency model 216 may train the one or more neural networks based on feedback associated with the urgency levels outputted by call urgency model 216 associated with communication sessions. In some examples, after call urgency model 216 determines the urgency level of a communication session based on contextual information, computing device 202 may output, at one or more output devices 246, an indication of the urgency level of the communication session and may prompt the user to confirm whether the urgency level determined by call urgency model 216 is accurate. If the user provides user input that indicates that the determined urgency level is not accurate, the user may also provide user input that indicates the actual urgency level. Computing device 152 may therefore input the accurate urgency level of the communication session at call urgency model 216 to train call urgency model 216.

In another example, computing device 202 may receive, in response to sending a request to establish a communication session and an indication of the urgency level of the communication session to a remote computing device, an indication of an accurate urgency level associated with the communication session from the remote computing device. Computing device 202 may therefore input the accurate urgency level of the communication session at call urgency model 216, and use the accurate urgency level to train the call urgency model 216 to more accurately determine the urgency level of a communication session. In some examples, if a particular critical event periodically occurs over a time interval (e.g., every hour), computing device 202 may train the one or more neural networks of call urgency model 216 to decrease the importance of the particular critical event in contributing to the determination of the urgency level.

Communication module 210 may therefore send, to a remote computing device, a request to establish a communication session along with contextual information indicative of the urgency level of the communication session. The contextual information may include an indication of the urgency level of the communication session. The contextual information may also include indications of health parameters of the user of computing device 202 such as the heart rate, the blood pressure, the oxygen saturation (SpO2) level, the stress level (e.g., electrodermal activity level), the blood glucose level, and the like, indications of the corresponding urgency levels of the health parameters of the user, the activity being performed by the user, the location of the user, one or more critical events of the user, and the like. In some examples, communication module 210 may also send, to the remote computing device, indications of contacts of one or more other remote computing devices to forward the communication session if the remote computing device determines to not accept the request to establish the communication session.

Communication module 210 may, in response to sending the request to establish the communication session to the remote computing device, receive, from the remote computing device, an indication of whether the remote computing device accepts the request to establish the communication session. Specifically, communication module 210 may receive one of: an indication that the remote computing device has accepted the request to establish the communication session or an indication that the remote computing device has declined the request to establish the communication session. For example, if the request to establish the communication session is a call made from computing device 202 to the remote device, the remote computing device may accept the request by accepting the call, and may decline or otherwise ignore the request by declining the call or otherwise ignoring or not answering the call.

If communication module 210 receives an indication that the remote computing device has accepted the request, communication module 210 may therefore establish the communication session with the remote computing device to enable the user of computing device 202 to communicate with the user of the remote device. In some examples, if communication module 160 receives an indication that the remote computing device has declined the request, communication module 210 may route the request to another remote computing device to establish the communication with the other remote computing device. In some examples, if communication module 160 receives an indication that the remote computing device has declined the request, communication module 210 may send messages (e.g., text messages) to one or more other computing devices to notify the one or more other devices that the remote computing device declined the request to establish the communication session and to notify the one or more other devices to the urgency level of the communication session.

In some examples, computing device 202 may further train the one or more neural networks of call urgency model 216 used to determine the urgency level of a communication session based on whether the remote computing device accepted the request to establish the communication session. For example, if the remote computing device does not accept the request to establish the communication session, communication module 210 may receive, from the remote computing device, information such as the activity of the user of remote computing device when the request to establish a communication session was received by the remote computing device. The activity of the user may indicate that the user is driving, at home, on a work call, and the like. Computing device 202 may therefore determine whether the user of the remote computing device was busy and not able to accept the request to establish the communication session. If the user of the remote computing device was busy and not able to accept the request to establish the communication session, then not accepting the request to establish the communication session may not be an indication that the urgency level of the communication session was incorrect. Conversely, if the user of the remote computing device was not busy, then not accepting the request to establish the communication session may be an indication that the urgency level of the communication session was incorrect. Computing device 202 may therefore train the one or more neural networks of call urgency model 216 based on such information received from the remote computing device.

In some examples, if the communication session was accepted by remote computing device, communication module 210 may receive, from the remote computing device, an indication of whether the user of the remote computing device indicated that the urgency level of the communication session was accurate. Computing device 202 may therefore train the one or more neural networks of call urgency model 216 based on such information received from the remote computing device.

In some examples, communication module 210 may receive requests to establish communication sessions from remote computing devices. When communication module 210 receives a request from a remote computing device to establish a communication session, a do not disturb feature of communication module 210 may, when active, prevent computing device 202 from outputting an indication of the request to establish the communication session.

When the do not disturb feature of computing device 102 is active and when the display of computing device 202 is off, communication module 210 may silence calls, alerts, and notifications by muting audio alerts, stopping haptic output (e.g., vibrations), and block visual disturbances from being outputted by one or more output devices 246 of computing device 202. That is, communication module 210 may, in response to receiving a request to establish a communication session, such as when communication module 210 receives a voice call or a video call, communication module 210 may cause one or more output devices 246 of computing device 202 to refrain from outputting an audible alert (e.g., a ringtone) and to refrain from outputting haptic output (e.g., vibrate) in response to receiving the request to establish a communication session.

In some examples, when the do not disturb feature of computing device 202 is active (i.e., turned on) and the display of computing device 202 is turned off, communication module 210 may, in response to receiving a request to establish a communication session, automatically decline the request without user intervention, such as by declining the call or sending a received call directly to voicemail. In some examples, when the do not disturb feature of computing device 202 is active, communication module 210 may, in response to receiving a request to establish a communication session, output a notification, such as at a display device of computing device 202, but may refrain from outputting an audible alert or haptic output indicative of computing device 202 receiving the request.

The user of computing device 202 may set up the do not disturb feature to be active in certain time periods and/or in certain contexts. For example, the user may set up the do not disturb feature to be active during certain time periods of the day, such as from 10:00 PM each night to 7:00 AM each morning so that the user will not be disturbed by computing device 202 ringing when the user is asleep. In another example, the user of computing device 202 may set up the do not disturb feature to automatically activate during the occurrence of events in an electronic calendar on computing device 202. In another example, communication module 210 may automatically activate, without user intervention, the do not disturb feature in response to computing device 202 determining that the user of computing device 202 is operating a motor vehicle (e.g., the user is driving).

When the do not disturb feature of computing device 202 is active and the display of computing device 202 is turned off, communication module 210 may, in response to receiving a request to establish a communication session, determine whether the request to establish a communication session meets a do not disturb exception. If communication module 210 determines that the request to establish the communication session meets a do not disturb exception, communication module 210 may enable the request to establish the communication session to bypass the do not disturb feature and to enable one or more output devices 246 to output an audible alert or to haptic output in response to receiving a request to establish a communication session to indicate the request. For example, when computing device 202 receives a call, the do not disturb exception may cause a speaker of computing device 202 to play a ringtone and/or may cause a vibration motor of computing device 202 to vibrate to provide haptic output to alert the user of computing device 202 to the call.

In some examples, a do not disturb exception corresponds to an urgency level of a communication session. Specifically, a do not disturb exception may be associated with an urgency level threshold, and a request to establish the communication session may meet the do not disturb exception if the urgency level of the communication session meets or exceeds (i.e., is greater than or equal to) the urgency level threshold. In the example where the urgency level of a communication session ranges from one to five, communication module 210 may determine that a do not disturb exception associated with an urgency level threshold of three, so that requests to establish communication sessions associated with urgency levels of three or higher may meet the do not disturb exception for communication module 210.

When the do not disturb feature of computing device 202 is active at computing device 202, communication module 210 may receive, from a remote computing device, a request to establish a communication session along with contextual information indicative of the urgency level of the communication session. Communication module 210 may, in response to receiving the request, determine, based at least in part on the contextual information, whether the request meets a do not disturb exception threshold to determine whether to bypass the do not disturb feature.

For example, if the contextual information indicative of the urgency level of the communication session indicates an urgency level of the communication session, communications module 210 may compare the urgency level of the communication session to an urgency level threshold associated with a do not disturb exception to determine whether to bypass the do not disturb feature of computing device 202. Specifically, communication module 210 may determine whether the urgency level of the communication session is greater than or equal to the urgency level threshold. Communication module 210 may determine that if the urgency level of the communication session is greater than or equal to the urgency level threshold, then the request to establish the communication session meets the do not disturb exception and may therefore bypass the do not disturb feature.

In some examples, a do not disturb exception corresponds to the user of the remote computing device being associated with at least one critical event. Communication module 210 may therefore determine that when the contextual information indicative of the urgency level of a communication session indicates at least one critical event associated with the user of the remote computing device, then the request to establish the communication session meets the do not disturb exception and may therefore bypass the do not disturb feature.

In some examples, a do not disturb exception corresponds to the corresponding urgency levels of the health parameters of the user of the remote computing device. For example, a do not disturb exception may be met if the corresponding urgency level of any of the health parameters of the user of the remote computing device is a four or a five when the range of values of the corresponding urgency levels is between one to five. Communication module 210 may therefore determine that when the contextual information indicative of the urgency level of a communication session indicates a corresponding urgency level of a health parameter having a value of four or a five, communication module 210, then the request to establish the communication session meets the do not disturb exception and may therefore bypass the do not disturb feature.

If communication module 210 determines that the request meets a do not disturb exception threshold and therefore determines to bypass the do not disturb feature, communication module 210 may, in response to determining to bypass the do not disturb feature, cause one or more output devices 246 to output an audible alert and/or haptic output that indicates the request to establish the communication session. In some examples, communication module 210 may, in response to determining to bypass the do not disturb feature, also cause one or more output devices 246 to output an indication of the urgency level of the communication session, such as at a display of computing device 202.

In some examples, communication module 210 may also receive from the remote computing device, along with the request to establish the communication session and the indication of the urgency level of the communication session, contextual information associated with the user of the remote computing device. Such contextual information may include indications of health parameters of the user of the remote computing device such as the heart rate, the blood pressure, the oxygen saturation (SpO2) level, the stress level (e.g., electrodermal activity level), the blood glucose level, and the like, indications of the corresponding urgency levels of the health parameters of the user, the activity being performed by the user, the location of the user, one or more critical events of the user, and the like. In some examples, communication module 210 may also receive, from the remote computing device, indications of contacts of one or more other remote computing devices to forward the communication session if the remote computing device determines to not accept the request to establish the communication session.

Communication module 210 may, in response to determining to bypass the do not disturb feature, also cause one or more output devices 246 to output the contextual information associated with the user of the remote computing device, such as at a display of computing device 202. For example, communication module 210 may output indications of the health parameters associated with the user of the remote computing device, indications of the corresponding urgency levels of the health parameters, an indication of the location of the user of the remote computing device, an indication of the one or more critical events associated with the user of the remote computing device, an indication of the activity being performed by the user of the remote computing device, and the like.

In some examples, in response to outputting an indication of the request to establish the communication with the remote computing device, computing device 202 may receive, at one or more input devices 242, user input that corresponds to accepting the request to establish the communication session or user input that corresponds to declining the request to establish the communication session. Communication module 210 may, in response to receiving user input that corresponds to accepting the request to establish the communication session, establish the communication session between the remote computing device and computing device 202.

Communication module 210 may, in response to receiving user input that corresponds to declining the request to establish the communication session, send, to the remote computing device, an indication that computing device 202 has declined the request to establish the communication session. In some examples, if communication module 210 has received, along with the request, an indication of one or more contacts from the remote computing device, communication module 210 may, in response to receiving user input that corresponds to declining the request to establish the communication session, forward the request to establish the communication session to another remote computing device associated with the one or more contacts or may send messages (e.g., text messages) to another remote computing device associated with the one or more contacts to notify the other remote computing device that computing device 202 has declined the request to establish the communication session and to notify the other remote computing device to the urgency level of the communication session.

In some examples, communication module 210 may determine the other computing device to which the request is forwarded based on the urgency level of the communication session. For example, each of the one or more contacts may be associated with a corresponding urgency level. Communication module 210 may determine, out of the one or more contacts, a contact associated with a corresponding urgency level that matches the urgency level of the communication session. Communication module 210 may therefore forward the request to establish the communication to the determined contact.

FIGS. 3A-3E illustrate example user interfaces that indicate requests to establish communication sessions, in accordance with aspects of the present disclosure. When the do not disturb feature of a computing device is active at the computing device, such as computing device 202, the computing device may, in response to receiving a request to establish a communication session, such as when the computing device receives a voice call or a video call, determine whether to bypass the do not disturb feature. The computing device may, in response to determining to bypass the do not disturb feature, output, for display at a display device, a user interface that indicates the request to establish the communication session and that indicates contextual information indicative of the urgency level of the request. Such a user interface may be an incoming call user interface outputted by the computing device at a display.

Figure 3A:
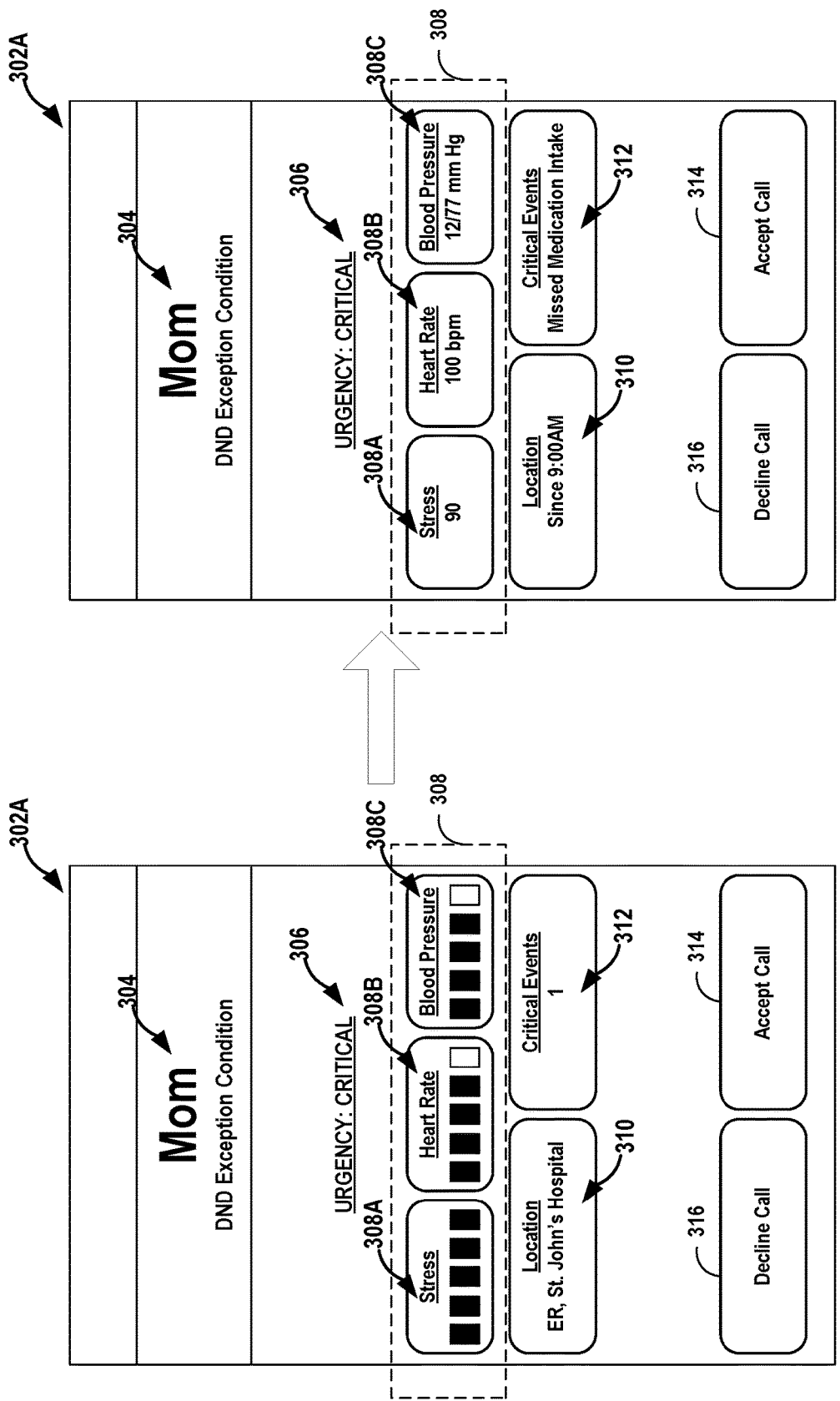
FIGS. 3A-3E illustrate example user interfaces that indicate requests to establish communication sessions, in accordance with aspects of the present disclosure.

As shown in FIG. 3A, an example indication of a request to establish a communication session outputted by a computing device may be in the form of user interface 302A, which may be an incoming call user interface outputted by a computing device in response to receiving, from a remote computing device the request to establish the communication session.

User interface 302A includes UI element 304 that indicates an identity of the user of the remote computing device that sent the request to establish the communication session. Such a user may be the caller that used the remote computing device to place the call to the computing device. In the example of FIG. 3A, UI element 304 may indicate the identity of the user of the remote computing device as "Mom."

User interface 302A also includes UI element 306 that indicates the urgency level of the communication session. In the example of FIG. 3A, UI element 306 may indicate the urgency level of the communication session as "Critical."

User interface 302A also includes UI elements 308A-308C ("UI elements 308") that indicate the health parameters of the user of the remote computing device that sent the request to establish the communication session. For example, UI element 308A indicates the corresponding urgency level associated with the stress level of the user of the remote computing device, UI element 308B indicates the corresponding urgency level associated with the heart rate of the user of the remote computing device, and UI element 308C indicates the corresponding urgency level associated with the blood pressure of the user of the remote computing device.

In some examples, user interface 302A may receive user input to toggle UI elements 308 between indicating the corresponding urgency levels of health parameters of the user of the remote device and indicating the values of the health parameters of the user of the remote device. For example, the computing device may receive user input that corresponds to selecting UI element 308A to toggle UI element 308A between indicating the corresponding urgency level associated with the stress level of the user of the remote computing device and the values of the stress level of the user of the remote computing device. Similarly, the computing device may receive user input that corresponds to selecting UI element 308B to toggle UI element 308B between indicating the corresponding urgency level associated with the heart rate of the user of the remote computing device and the values of the heart rate of the user of the remote computing device. The computing device may receive user input that corresponds to selecting UI element 308C to toggle UI element 308C between indicating the corresponding urgency level associated with the blood pressure of the user of the remote computing device and the values of the blood pressure of the user of the remote computing device.

User interface 302A also includes UI element 310 that indicates the location of the user of the remote computing device. In the example of FIG. 3A, UI element 310 may indicate the location of the user of the remote computing device as in the emergency room of St. John's hospital. In some examples, user interface 302A may receive user input to toggle UI element 310 between indicating the location of the user of the remote computing device and indicating the amount of time the user of the remote computing device has spent at the location. For example, the computing device may receive user input that corresponds to selecting UI element 310 to toggle UI element 310 between indicating the location of the user of the remote computing device as the emergency room of St. John's hospital and an indication that the user of the remote computing device has been at the emergency room of St. John's hospital since 9:00 AM.

User interface 302A also includes UI element 312 that indicates the critical events associated with the user of the remote computing device. For example, UI element 312 may indicate the number of critical events associated with the user of the remote device. In some examples, user interface 302A may receive user input to toggle UI element 312 between indicating the number of critical events associated with the user of the remote computing device and indicating information associated with critical events associated with the user of the remote computing device. For example, the computing device may receive user input that corresponds to selecting UI element 312 to toggle UI element 312 between indicating the user of the remote computing device being associated with one critical event and an indication that the one critical event associated with the user of the remote computing device is the user of the remote computing device missed taking medication.

User interface 302A also includes UI controls 314 and 316 that the user of the computing device may provide user input to accept the request to establish the communication session or to decline the request to establish the communication session. In the example where the request to establish the communication session is a request to accept a call, UI control 314 may be an accept call button that can be selected to accept the call and UI control 316 may be a decline call button that can be selected to decline the call.

Figure 3B:
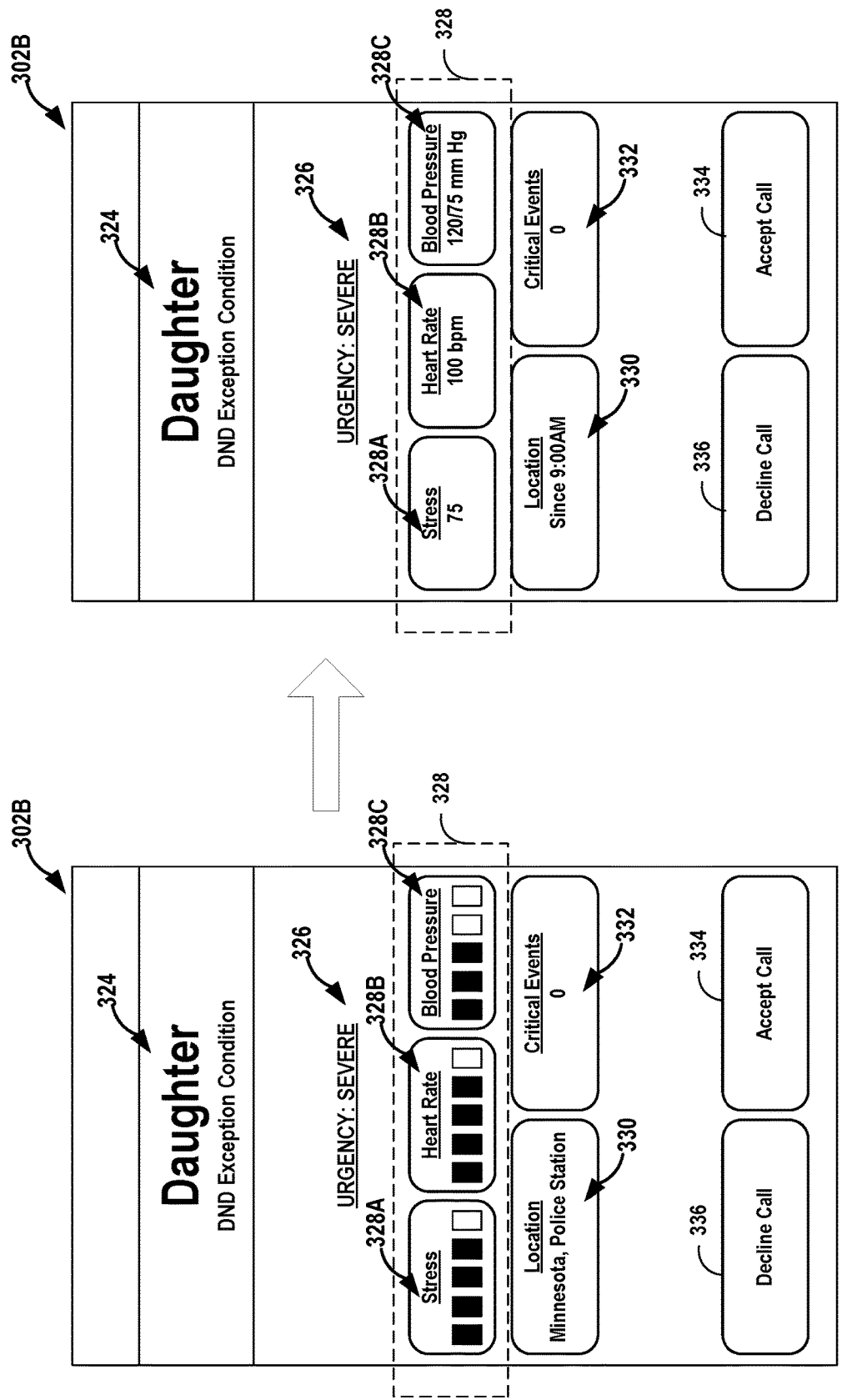

As shown in FIG. 3B, an example indication of a request to establish a communication session outputted by a computing device may be in the form of user interface 302B, which may be an incoming call user interface outputted by a computing device in response to receiving, from a remote computing device the request to establish the communication session.

User interface 302B includes UI element 324 that indicates an identity of the user of the remote computing device that sent the request to establish the communication session. Such a user may be the caller that used the remote computing device to place the call to the computing device. In the example of FIG. 3B, UI element 324 may indicate the identity of the user of the remote computing device as "Daughter."

User interface 302B also includes UI element 326 that indicates the urgency level of the communication session. In the example of FIG. 3B, UI element 326 may indicate the urgency level of the communication session as "Severe."

User interface 302B also includes UI elements 328A-328C ("UI elements 328") that indicate the health parameters of the user of the remote computing device that sent the request to establish the communication session. For example, UI element 328A indicates the corresponding urgency level associated with the stress level of the user of the remote computing device, UI element 328B indicates the corresponding urgency level associated with the heart rate of the user of the remote computing device, and UI element 328C indicates the corresponding urgency level associated with the blood pressure of the user of the remote computing device.

In some examples, user interface 302B may receive user input to toggle UI elements 328 between indicating the corresponding urgency levels of health parameters of the user of the remote device and indicating the values of the health parameters of the user of the remote device. For example, the computing device may receive user input that corresponds to selecting UI element 328A to toggle UI element 328A between indicating the corresponding urgency level associated with the stress level of the user of the remote computing device and the values of the stress level of the user of the remote computing device. Similarly, the computing device may receive user input that corresponds to selecting UI element 328B to toggle UI element 328B between indicating the corresponding urgency level associated with the heart rate of the user of the remote computing device and the values of the heart rate of the user of the remote computing device. The computing device may receive user input that corresponds to selecting UI element 328C to toggle UI element 328C between indicating the corresponding urgency level associated with the blood pressure of the user of the remote computing device and the values of the blood pressure of the user of the remote computing device.

User interface 302B also includes UI element 330 that indicates the location of the user of the remote computing device. In the example of FIG. 3B, UI element 330 may indicate the location of the user of the remote computing device as in a police station in Minnesota. In some examples, user interface 302B may receive user input to toggle UI element 330 between indicating the location of the user of the remote computing device and indicating the amount of time the user of the remote computing device has spent at the location. For example, the computing device may receive user input that corresponds to selecting UI element 330 to toggle UI element 330 between indicating the location of the user of the remote computing device as a police station in Minnesota and an indication that the user of the remote computing device has been at the police station in Minnesota since 9:00 AM.

User interface 302B also includes UI element 332 that indicates the critical events associated with the user of the remote computing device. For example, UI element 332 may indicate the number of critical events associated with the user of the remote device.

User interface 302B also includes UI controls 334 and 336 that the user of the computing device may provide user input to accept the request to establish the communication session or to decline the request to establish the communication session. In the example where the request to establish the communication session is a request to accept a call, UI control 334 may be an accept call button that can be selected to accept the call and UI control 336 may be a decline call button that can be selected to decline the call.

Figure 3C:
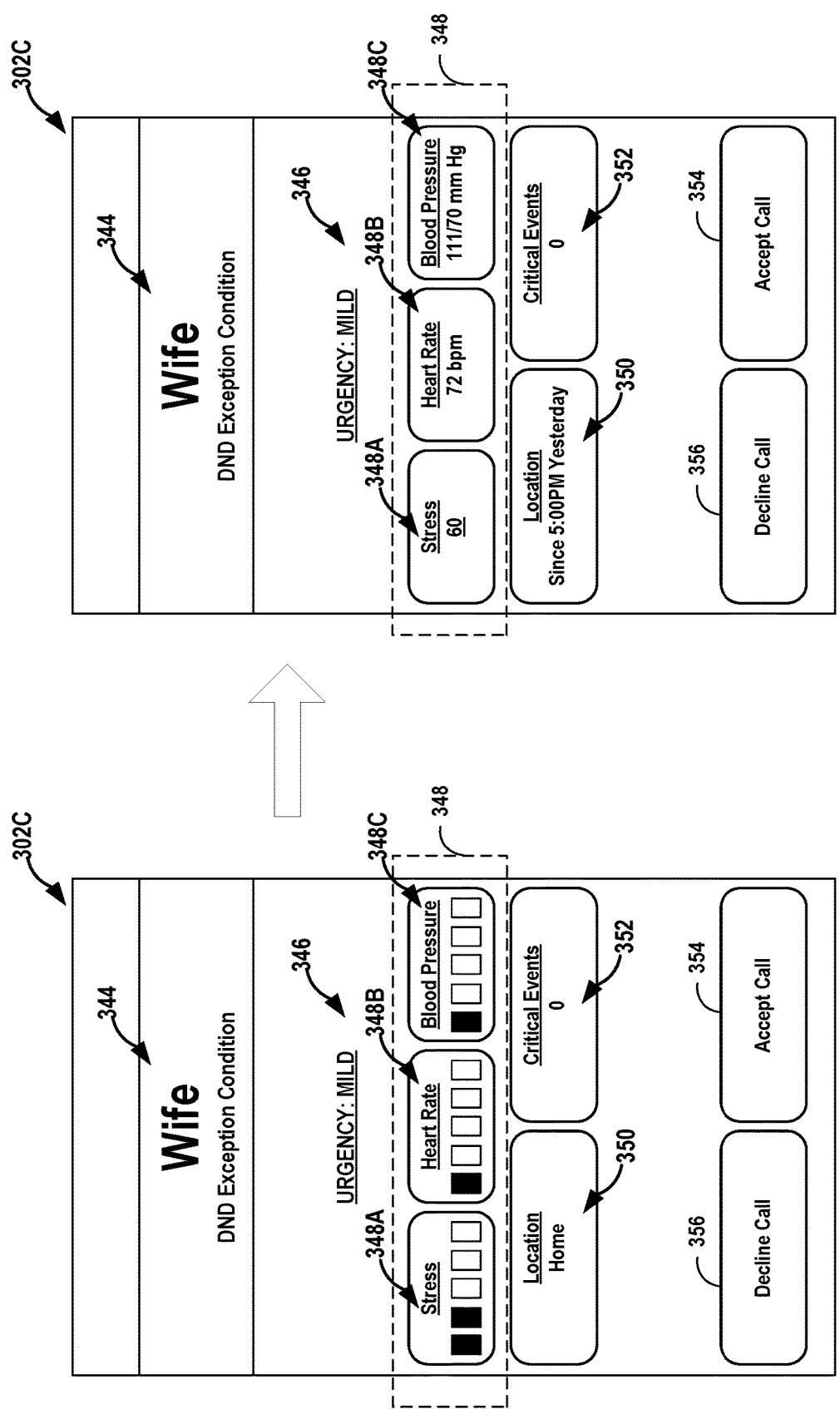

As shown in FIG. 3C, an example indication of a request to establish a communication session outputted by a computing device may be in the form of user interface 302C, which may be an incoming call user interface outputted by a computing device in response to receiving, from a remote computing device the request to establish the communication session.

User interface 302C includes UI element 344 that indicates an identity of the user of the remote computing device that sent the request to establish the communication session. Such a user may be the caller that used the remote computing device to place the call to the computing device. In the example of FIG. 3C, UI element 344 may indicate the identity of the user of the remote computing device as "Wife."

User interface 302C also includes UI element 346 that indicates the urgency level of the communication session. In the example of FIG. 3C, UI element 346 may indicate the urgency level of the communication session as "Mild."

User interface 302C also includes UI elements 348A-348C ("UI elements 348") that indicate the health parameters of the user of the remote computing device that sent the request to establish the communication session. For example, UI element 348A indicates the corresponding urgency level associated with the stress level of the user of the remote computing device, UI element 348B indicates the corresponding urgency level associated with the heart rate of the user of the remote computing device, and UI element 348C indicates the corresponding urgency level associated with the blood pressure of the user of the remote computing device.

In some examples, user interface 302C may receive user input to toggle UI elements 348 between indicating the corresponding urgency levels of health parameters of the user of the remote device and indicating the values of the health parameters of the user of the remote device. For example, the computing device may receive user input that corresponds to selecting UI element 348A to toggle UI element 348A between indicating the corresponding urgency level associated with the stress level of the user of the remote computing device and the values of the stress level of the user of the remote computing device. Similarly, the computing device may receive user input that corresponds to selecting UI element 348B to toggle UI element 348B between indicating the corresponding urgency level associated with the heart rate of the user of the remote computing device and the values of the heart rate of the user of the remote computing device. The computing device may receive user input that corresponds to selecting UI element 348C to toggle UI element 348C between indicating the corresponding urgency level associated with the blood pressure of the user of the remote computing device and the values of the blood pressure of the user of the remote computing device.

User interface 302C also includes UI element 350 that indicates the location of the user of the remote computing device. In the example of FIG. 3C, UI element 350 may indicate the location of the user of the remote computing device as being at home. In some examples, user interface 302C may receive user input to toggle UI element 350 between indicating the location of the user of the remote computing device and indicating the amount of time the user of the remote computing device has spent at the location. For example, the computing device may receive user input that corresponds to selecting UI element 350 to toggle UI element 350 between indicating the location of the user of the remote computing device as being at home and an indication that the user of the remote computing device has been at home since 5:00 PM yesterday.

User interface 302C also includes UI element 352 that indicates the critical events associated with the user of the remote computing device. For example, UI element 352 may indicate the number of critical events associated with the user of the remote device.

User interface 302C also includes UI controls 354 and 356 that the user of the computing device may provide user input to accept the request to establish the communication session or to decline the request to establish the communication session. In the example where the request to establish the communication session is a request to accept a call, UI control 354 may be an accept call button that can be selected to accept the call and UI control 356 may be a decline call button that can be selected to decline the call.

Figure 3D:
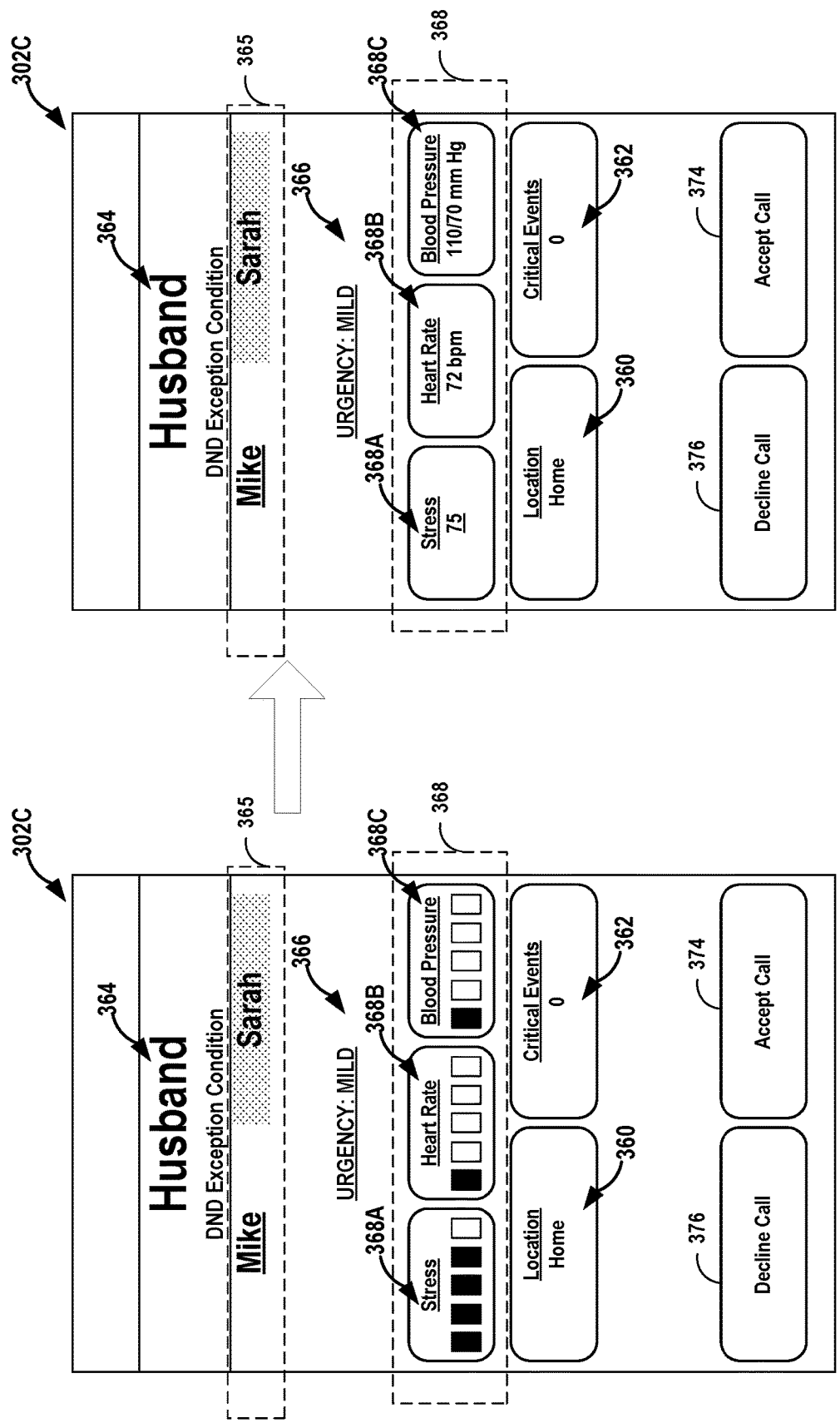

As shown in FIG. 3D, an example indication of a request to establish a communication session outputted by a computing device may be in the form of user interface 302D, which may be an incoming call user interface outputted by a computing device in response to receiving, from a remote computing device the request to establish the communication session.

User interface 302D includes UI element 364 that indicates an identity of the user of the remote computing device that sent the request to establish the communication session. Such a user may be the caller that used the remote computing device to place the call to the computing device. In the example of FIG. 3D, UI element 364 may indicate the identity of the user of the remote computing device as "Husband."

The computing device may receive, along with the request to establish the communication session, contextual information associated with both the user of the remote computing device that sent the request as well as the contextual information associated with another user that has authorized sharing their contextual information to the user of the remote computing device and to the user of the computing device. For example, the user of the remote computing device may be the husband of the user of the computing device named "Mike", and the computing device may receive contextual information associated with both the user "Mike" of the remote computing device that sent the request as well as the contextual information associated with another user "Sarah" to Mike. For example, Sarah may be the daughter of Mike as well as the daughter of the user of the computing device.

Thus, user interface 302D may include UI element 365 that enables the user to toggle between viewing contextual information associated with the user "Mike" as well as the contextual information associated with the user "Sarah." User interface 302D may highlight the user associated with the higher urgency level out of the two users. In the example of FIG. 302D, user interface 302D may highlight the user "Sarah" as having the higher urgency level out of the users "Mike" and "Sarah." For example, UI element 365 may highlight the name "Sarah" to indicate that the user "Sarah" as having the higher urgency level.

In the example of FIG. 3D, UI element 365 has been toggled to select the user "Mike" so that user interface 302D presents the contextual information associated with the user "Mike." User interface 302D also includes UI element 366 that indicates the urgency level associated with the user "Mike." In the example of FIG. 3D, UI element 366 may indicate the urgency level as "Mild." User interface 302D also includes UI elements 368A-368C ("UI elements 368") that indicate the health parameters of the user "Mike." For example, UI element 368A indicates the corresponding urgency level associated with the stress level of the user "Mike," UI element 368B indicates the corresponding urgency level associated with the heart rate of the user "Mike," and UI element 368C indicates the corresponding urgency level associated with the blood pressure of the user "Mike."

In some examples, user interface 302D may receive user input to toggle UI elements 368 between indicating the corresponding urgency levels associated with health parameters of the user "Mike" and indicating the values of the health parameters of the user "Mike." For example, the computing device may receive user input that corresponds to selecting UI element 368A to toggle UI element 368A between indicating the corresponding urgency level associated with the stress level of the user "Mike" and the values of the stress level of the user "Mike." Similarly, the computing device may receive user input that corresponds to selecting UI element 368B to toggle UI element 368B between indicating the corresponding urgency level associated with the heart rate of the user "Mike" and the values of the heart rate of the user "Mike." The computing device may receive user input that corresponds to selecting UI element 368C to toggle UI element 368C between indicating the corresponding urgency level associated with the blood pressure of the user "Mike" and the values of the blood pressure of the user "Mike."

User interface 302D also includes UI element 360 that indicates the location of the user "Mike." In the example of FIG. 3D, UI element 360 may indicate the location of the user "Mike" as being at home. User interface 302D also includes UI element 362 that indicates the critical events associated with the user "Mike." For example, UI element 362 may indicate the number of critical events associated with the user "Mike."

User interface 302D also includes UI controls 374 and 376 that the user of the computing device may provide user input to accept the request to establish the communication session or to decline the request to establish the communication. In the example where the request to establish the communication session is a request to accept a call, UI control 374 may be an accept call button that can be selected to accept the call and UI control 376 may be a decline call button that can be selected to decline the call.

Figure 3E:
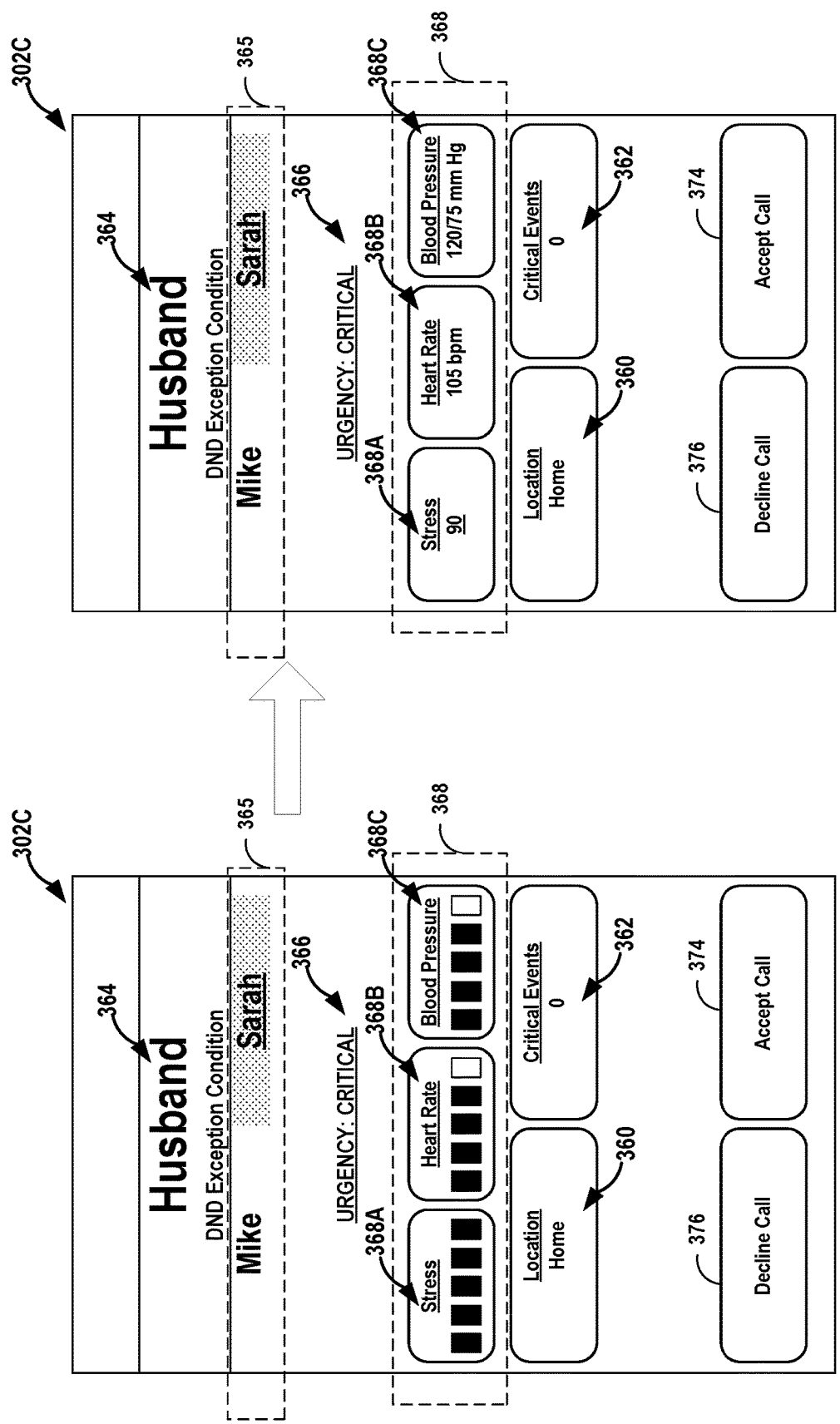

As shown in FIG. 3E, continuing from FIG. 3D, UI element 365 has been toggled to select the user "Sarah" so that user interface 302D presents the contextual information associated with the user "Sarah."

User interface 302D also includes UI element 366 that indicates the urgency level associated with the user "Sarah." In the example of FIG. 3D, UI element 366 may indicate the urgency level as "Critical." User interface 302D also includes UI elements 368A-368C ("UI elements 368") that indicate the health parameters of the user "Sarah." For example, UI element 368A indicates the corresponding urgency level associated with the stress level of the user "Sarah," UI element 368B indicates the corresponding urgency level associated with the heart rate of the user "Sarah," and UI element 368C indicates the corresponding urgency level associated with the blood pressure of the user "Sarah."

In some examples, user interface 302D may receive user input to toggle UI elements 368 between indicating the corresponding urgency levels associated with health parameters of the user "Sarah" and indicating the values of the health parameters of the user "Sarah." For example, the computing device may receive user input that corresponds to selecting UI element 368A to toggle UI element 368A between indicating the corresponding urgency level associated with the stress level of the user "Sarah" and the values of the stress level of the user "Sarah." Similarly, the computing device may receive user input that corresponds to selecting UI element 368B to toggle UI element 368B between indicating the corresponding urgency level associated with the heart rate of the user "Sarah" and the values of the heart rate of the user "Sarah." The computing device may receive user input that corresponds to selecting UI element 368C to toggle UI element 368C between indicating the corresponding urgency level associated with the blood pressure of the user "Sarah" and the values of the blood pressure of the user "Sarah."

User interface 302D also includes UI element 360 that indicates the location of the user "Sarah." In the example of FIG. 3D, UI element 360 may indicate the location of the user "Sarah" as being at home. User interface 302D also includes UI element 362 that indicates the critical events associated with the user "Sarah." For example, UI element 362 may indicate the number of critical events associated with the user "Sarah."

Figure 4:
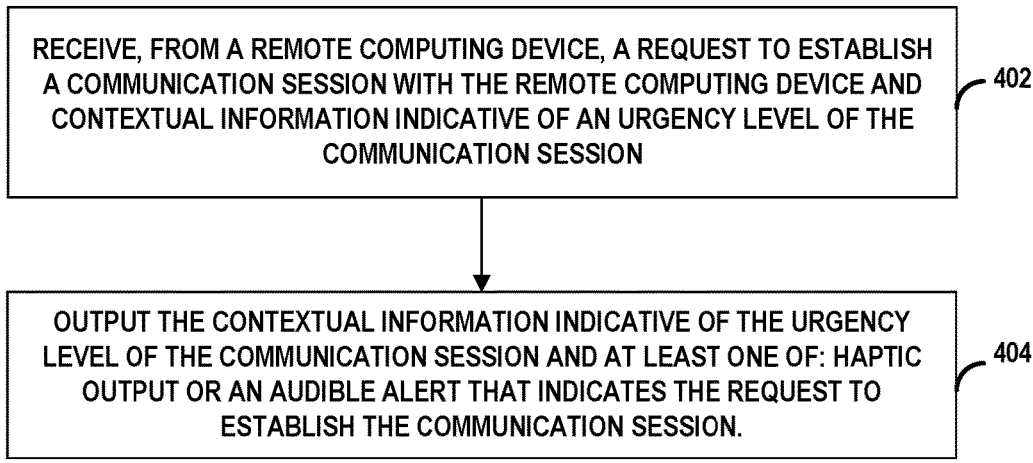
FIG. 4 is a flowchart illustrating an example mode of operation for a computing device in accordance with one or more techniques of the present disclosure.

FIG. 4 is a flowchart illustrating an example mode of operation for a computing device in accordance with one or more techniques of the present disclosure. FIG. 4 is described below in the context of computing device 202 of FIG. 2.

As shown in FIG. 4, a computing device 202 may receive, from a remote computing device, a request to establish a communication session with the remote computing device and contextual information indicative of an urgency level of the communication session (402). Next, the computing device 202 may output the contextual information indicative of the urgency level of the communication session and at least one of: haptic output or an audible alert that indicates the request to establish the communication session (404).

In some examples, the contextual information indicates an urgency level of the communication session, and computing device 202 may determine whether to bypass the do not disturb feature of the computing device 202 by comparing the urgency level of the communication session with an urgency level threshold associated with a do not disturb exception to determine whether to bypass the do not disturb feature of the computing device.

In some examples, computing device 202 may, in response to determining to bypass the do not disturb feature of the computing device 202, output an indication of the request to establish the communication session that indicates at least the urgency level of the communication session.

In some examples, the urgency level of the communication session is determined based at least in part on health parameters of a user of the remote computing device. In some examples, the health parameters of the user include one or more of: a stress level of the user, a blood pressure of the user, or a heart rate of the user, an oxygen saturation level of the user, or a blood glucose level of the user. In some examples, the urgency level of the communication session is determined based at least in part on corresponding urgency levels of the health parameters of the user of the remote computing device. In some examples, the urgency level of the communication session is determined based at least in part on one or more critical events associated with the user.

In some examples, computing device 202 may further receive user input indicative of an accuracy of the urgency level of the communication session and may send, to the remote computing device, an indication of the accuracy of the urgency level of the communication session.

In some examples, computing device 202 may receive user input that corresponds to accepting the request to establish the communication session and may, in response to accepting the user input that corresponds to accepting the request to establish the communication session, establish the communication session with the remote computing device.

In some examples, the communication session comprises one of a voice call or a video call.

Figure 5:
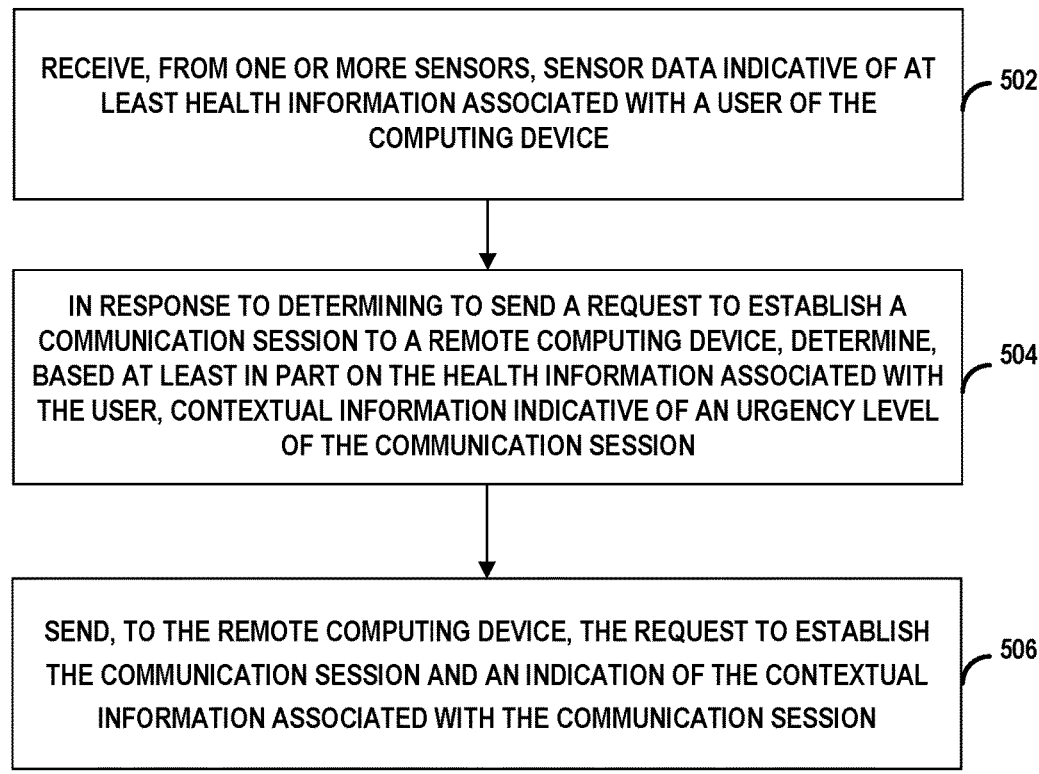
FIG. 5 is a flowchart illustrating an example mode of operation for a computing device in accordance with one or more techniques of the present disclosure.

FIG. 5 is a flowchart illustrating an example mode of operation for a computing device in accordance with one or more techniques of the present disclosure. FIG. 5 is described below in the context of computing device 202 of FIG. 2.

As shown in FIG. 5, computing device 202 may receive, from one or more sensors, sensor data indicative of at least health information associated with a user of the computing device (502). Computing device 202 may, in response to determining to send a request to establish a communication session to a remote computing device, determine, based at least in part on the health information associated with the user, contextual information indicative of an urgency level of the communication session (504). Computing device 202 may send, to the remote computing device, the request to establish the communication session and an indication of the urgency level of the communication session (506).

In some examples, to receive, from the one or more sensors, computing device 202 may receive, from the one or more sensors of a wearable computing device of the user of the computing device, the sensor data. In some examples, the one or more sensors includes one or more of: a heart rate sensor, a blood pressure sensor, an oxygen saturation sensor, a glucose sensor, or an electrodermal activity sensor.

In some examples, computing device 202 may further determine, based at least in part on the sensor data, health parameters associated with the user, wherein the health parameters comprise one or more of: heart rate of the user, blood pressure of the user, oxygen saturation of the user, glucose level of the user, or stress of the user, and determine an urgency level of the communication session based at least in part on the health parameters associated with the user.

In some examples, computing device 202 may determine, for each of the health parameters, a corresponding urgency level, wherein to determine, based at least in part on the health parameters associated with the user, the urgency level of the communication session, the computing device 202 may determine, based at least in part on the corresponding urgency level of each of the health parameters, the urgency level of the communication session.

In some examples, to determine, for each of the health parameters, the corresponding urgency level, computing device 202 may compare health information associated with a health parameter of the health parameters collected over an immediately preceding period of time with a baseline level associated with the health parameter to determine the corresponding urgency level of the health parameter.

In some examples, computing device 202 may determine one or more critical events associated with the user, where to determine the urgency level of the communication session, computing device 202 may determine, based at least in part on the one or more critical events, the urgency level of the communication session.

In some examples, to determine the urgency level of the communication session, computing device 202 may use a machine trained model, the urgency level of the communication session.

In some examples, computing device 202 may receive, from the remote computing device, an indication of an actual urgency level of the communication session. Computing device 202 may train the machine trained model using the actual urgency level of the communication session.

In some examples, the communication session is one of: a voice call or an audio call.

This disclosure contains the following examples:

Example 1: A method includes while receiving, by the computing device from a remote computing device, a request to establish a communication session with the remote computing device and contextual information indicative of an urgency level of the communication session; determining, by the computing device and based at least in part on the contextual information indicative of the urgency level of the communication session, whether to bypass the do not disturb feature of the computing device; and outputting, by the computing device, the contextual information indicative of the urgency level of the communication session and at least one of: haptic output or an audible alert that indicates the request to establish the communication session.

Example 2: The method of example 1, wherein: receiving the request to establish the communication session with the remote computing device and the contextual information indicative of the urgency level of the communication session further comprises while a do not disturb feature of the computing device is active at the computing device, receiving, by the computing device from the remote computing device, the request to establish the communication session with the remote computing device and the contextual information indicative of the urgency level of the communication session; and outputting the contextual information indicative of the urgency level of the communication session further comprises: determining, by the computing device and based at least in part on the contextual information indicative of the urgency level of the communication session, whether to bypass the do not disturb feature of the computing device, and in response to determining to bypass the do not disturb feature of the computing device, outputting, by the computing device, the contextual information indicative of the urgency level of the communication session and at least one of: the haptic output or the audible alert that indicates the request to establish the communication session.

Example 3: The method of example 2, wherein determining whether to bypass the do not disturb feature of the computing device further comprises: comparing, by the computing device, the urgency level of the communication session with an urgency level threshold associated with a do not disturb exception to determine whether to bypass the do not disturb feature of the computing device.

Example 4: The method of example 3, further includes in response to determining to bypass the do not disturb feature of the computing device, outputting, by the computing device, an indication of the request to establish the communication session that indicates at least the urgency level of the communication session.

Example 5: The method of any of examples 1-4, wherein the urgency level of the communication session is determined based at least in part on health parameters of a user, wherein the user uses the remote computing device or is another person.

Example 6: The method of example 5, wherein the health parameters of the user include one or more of: a stress level of the user, a blood pressure of the user, or a heart rate of the user, an oxygen saturation level of the user, or a blood glucose level of the user.

Example 7: The method of any of examples 5 and 6, wherein the urgency level of the communication session is determined based at least in part on corresponding urgency levels of the health parameters of the user of the remote computing device.

Example 8: The method of any of examples 1-7, wherein the urgency level of the communication session is determined based at least in part on one or more critical events associated with the user.

Example 9: The method of any of examples 1-8, further includes receiving, by the computing device, user input indicative of an accuracy of the urgency level of the communication session; sending, by the computing device to the remote computing device, an indication of the accuracy of the urgency level of the communication session.

Example 10: The method of any of examples 1-9, further includes receiving, by the computing device, user input that corresponds to accepting the request to establish the communication session; and in response to accepting the user input that corresponds to accepting the request to establish the communication session, establishing, by the computing device, the communication session with the remote computing device.

Example 11: The method of any of examples 1-10, wherein the communication session comprises one of a voice call or a video call.

Example 12: A computing device includes one or more output devices; and one or more processors configured to: receive, from a remote computing device, a request to establish a communication session with the remote computing device and contextual information indicative of an urgency level of the communication session; and output, at the one or more output devices, the contextual information indicative of the urgency level of the communication session and at least one of: haptic output or an audible alert that indicates the request to establish the communication session.

Example 13: The computing device of example 12, wherein: to receive, from the remote computing device, the request to establish the communication session with the remote computing device and the contextual information indicative of the urgency level of the communication session, the one or more processors are further configured to, while a do not disturb feature of the computing device is active at the computing device, receive, from the remote computing device, the request to establish the communication session with the remote computing device and the contextual information indicative of the urgency level of the communication session; and to output the contextual information indicative of the urgency level of the communication session, the one or more processors are further configured to: determine, based at least in part on the contextual information indicative of the urgency level of the communication session, whether to bypass the do not disturb feature of the computing device, and in response to determining to bypass the do not disturb feature of the computing device, output the contextual information indicative of the urgency level of the communication session and at least one of: the haptic output or the audible alert that indicates the request to establish the communication session.

Example 14: The computing device of example 13, wherein to determine whether to bypass the do not disturb feature of the computing device, the one or more processors are further configured to: compare the urgency level of the communication session with an urgency level threshold associated with a do not disturb exception to determine whether to bypass the do not disturb feature of the computing device.

Example 15: The computing device of example 14, wherein the one or more processors are further configured to: in response to determining to bypass the do not disturb feature of the computing device, output, at the one or more output devices, an indication of the request to establish the communication session that indicates at least the urgency level of the communication session.

Example 16: The computing device of any of examples 12-15, wherein the urgency level of the communication session is determined based at least in part on health parameters of a user, wherein the user uses the remote computing device or is another person.

Example 17: The computing device of example 16, wherein the health parameters of the user include one or more of: a stress level of the user, a blood pressure of the user, or a heart rate of the user, an oxygen saturation level of the user, or a blood glucose level of the user.

Example 18: The computing device of any of examples 16 and 17, wherein the urgency level of the communication session is determined based at least in part on corresponding urgency levels of the health parameters of the user.

Example 19: The computing device of any of examples 12-18, wherein the urgency level of the communication session is determined based at least in part on one or more critical events associated with the user.

Example 20: A computer-readable storage medium storing instructions that, when executed, cause one or more processors of a computing device to: receive, from a remote computing device, a request to establish a communication session with the remote computing device and contextual information indicative of an urgency level of the communication session; and output, at one or more output devices, the contextual information indicative of the urgency level of the communication session and at least one of: haptic output or an audible alert that indicates the request to establish the communication session.

Example 21: A method includes receiving, by a computing device from one or more sensors, sensor data indicative of at least health information associated with a user of the computing device; in response to determining to send a request to establish a communication session to a remote computing device, determining, by the computing device and based at least in part on the health information associated with the user, contextual information indicative of an urgency level of the communication session; sending, by the computing device to the remote computing device, the request to establish the communication session and an indication of the urgency level of the communication session.

Example 22: The method of example 21, wherein receiving, from the one or more sensors, the sensor data further comprises receiving, by the computing device and from the one or more sensors of a wearable computing device of the user of the computing device, the sensor data.

Example 23: The method of example 22, wherein the one or more sensors includes one or more of: a heart rate sensor, a blood pressure sensor, an oxygen saturation sensor, a glucose sensor, or an electrodermal activity sensor.

Example 24: The method of any of examples 22 and 23, further includes determining, by the computing device and based at least in part on the sensor data, health parameters associated with the user, wherein the health parameters comprise one or more of: heart rate of the user, blood pressure of the user, oxygen saturation of the user, glucose level of the user, or stress of the user; and determining, by the computing device, the urgency level of the communication session based at least in part on the health parameters associated with the user.

Example 25: The method of example 24, further includes determining, by the computing device and for each of the health parameters, a corresponding urgency level, wherein determining, based at least in part on the health parameters associated with the user, the urgency level of the communication session further includes determining, by the computing device and based at least in part on the corresponding urgency level of each of the health parameters, the urgency level of the communication session.

Example 26: The method of example 25, wherein determining, for each of the health parameters, the corresponding urgency level further comprises: comparing health information associated with a health parameter of the health parameters collected over an immediately preceding period of time with a baseline level associated with the health parameter to determine the corresponding urgency level of the health parameter.

Example 27: The method of any of examples 25 and 26, further includes determining, by the computing device, one or more critical events associated with the user; wherein determining the urgency level of the communication session further includes determining, by the computing device and based at least in part on the one or more critical events, the urgency level of the communication session.

Example 28: The method of example 27, wherein determining the urgency level of the communication session comprises determining, by the computing device using a machine trained model, the urgency level of the communication session.

Example 29: The method of example 28, further includes receiving, from the remote computing device an indication of an actual urgency level of the communication session; and training, by the computing device, the machine trained model using the actual urgency level of the communication session.

Example 30: The method of any of examples 21-29, wherein the communication session is one of: a voice call or an audio call.

Example 31: A computing device includes one or more sensors configured to sense at least health information associated with a user of the computing device; and one or more processors configured to: receive, from at least the one or more sensors, sensor data; in response to determining to send a request to establish a communication session to a remote computing device, determine, based at least in part on the health information associated with the user, contextual information indicative of an urgency level of the communication session; and send, to the remote computing device, the request to establish the communication session and an indication of the urgency level of the communication session.

Example 32: The computing device of example 31, wherein to receive the sensor data, the one or more processors are further configured to receive, from a wearable computing device of the user, the sensor data provided by a second one or more sensors of the wearable computing device.

Example 33: The computing device of example 32, wherein the one or more sensors and the second one or more sensors include one or more of: a heart rate sensor, a blood pressure sensor, an oxygen saturation sensor, a glucose sensor, or an electrodermal activity sensor.

Example 34: The computing device of any of examples 32 and 33, wherein the one or more processors are further configured to: determine, based at least in part on the sensor data, health parameters associated with the user, wherein the health parameters comprise one or more of: heart rate of the user, blood pressure of the user, oxygen saturation of the user, glucose level of the user, or stress of the user; and determine an urgency level of the communication session based at least in part on the health parameters associated with the user.

Example 35: The computing device of example 34, wherein the one or more processors are further configured to: determine, for each of the health parameters, a corresponding urgency level, wherein to determine, based at least in part on the health parameters associated with the user, the urgency level of the communication session, the one or more processors are further configured to determine, based at least in part on the corresponding urgency level of each of the health parameters, the urgency level of the communication session.

Example 36: The computing device of example 35, wherein to determine, for each of the health parameters, the corresponding urgency level, the one or more processors are further configured to: compare health information associated with a health parameter of the health parameters collected over an immediately preceding period of time with a baseline level associated with the health parameter to determine the corresponding urgency level of the health parameter.

Example 37: The computing device of any of examples 35 and 36, wherein the one or more processors are further configured to: determine one or more critical events associated with the user, wherein to determine the urgency level of the communication session, the one or more processors are further configured to determine, based at least in part on the one or more critical events, the urgency level of the communication session.

Example 38: The computing device of example 37, wherein to determine an urgency level of the communication session, the one or more processors are further configured to determine, using a machine trained model, the urgency level of the communication session.

Example 39: The computing device of example 38, wherein the one or more processors are further configured to: receive an indication of an actual urgency level of the communication session; and train the machine trained model using the actual urgency level of the communication session.

Example 40: A computer-readable storage medium storing instructions that, when executed, cause one or more processors of a computing device to: receive, from one or more sensors, sensor data; in response to determining to send a request to establish a communication session to a remote computing device, determine, based at least in part on the health information associated with the user, contextual information indicative of an urgency level of the communication session; and send, to the remote computing device, the request to establish the communication session and an indication of the urgency level of the communication session.

By way of example, and not limitation, such computer-readable storage media can comprise RAM, ROM, EEPROM, CD-ROM or other optical disk storage, magnetic disk storage, or other magnetic storage devices, flash memory, or any other storage medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage mediums and media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable medium.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various embodiments have been described. These and other embodiments are within the scope of the following claims.

What is claimed is:

1. A computer-implemented method comprising:
   receiving, by one or more processors of a computing device from a remote computing device, while a do not disturb feature of the computing device is active at the computing device, a request to establish a communication session with the remote computing device and contextual information indicative of an urgency level of the communication session;
   determining, by the one or more processors and based at least in part on the contextual information indicative of the urgency level of the communication session, to bypass the do not disturb feature of the computing device; and
   in response to determining to bypass the do not disturb feature of the computing device, outputting, by the one or more processors, the contextual information indicative of the urgency level of the communication session and at least one of: haptic output or an audible alert that indicates the request to establish the communication session.

2. The computer-implemented method of claim 1, wherein determining whether to bypass the do not disturb feature of the computing device further comprises:
   comparing, by the one or more processors, the urgency level of the communication session with an urgency level threshold associated with a do not disturb exception to determine whether to bypass the do not disturb feature of the computing device.

3. The computer-implemented method of claim 2, further comprising:
   in response to determining to bypass the do not disturb feature of the computing device, outputting, by the one or more processors, an indication of the request to establish the communication session that indicates at least the urgency level of the communication session.

4. The computer-implemented method of claim 1, wherein the urgency level of the communication session is based at least in part on health parameters of a user, wherein the user uses the remote computing device or is another person.

5. The computer-implemented method of claim 4, wherein the health parameters of the user include one or more of: a stress level of the user, a blood pressure of the user, a heart rate of the user, an oxygen saturation level of the user, or a blood glucose level of the user.

6. The computer-implemented method of claim 4, wherein the urgency level of the communication session is based at least in part on corresponding urgency levels of the health parameters of the user.

7. The computer-implemented method of claim 1, wherein the urgency level of the communication session is determined based at least in part on one or more critical events associated with a user of the remote computing device.

8. The computer-implemented method of claim 1, further comprising:
   receiving, by the one or more processors, user input indicative of an accuracy of the urgency level of the communication session; and
   sending, by the one or more processors to the remote computing device, an indication of the accuracy of the urgency level of the communication session.

9. The computer-implemented method of claim 1, further comprising:
   receiving, by the one or more processors, user input that corresponds to accepting the request to establish the communication session; and
   in response to accepting the user input that corresponds to accepting the request to establish the communication session, establishing, by the one or more processors, the communication session with the remote computing device.

10. The computer-implemented method of claim 1, wherein the communication session comprises one of a voice call or a video call.

11. A computing device comprising:
    one or more output devices; and
    one or more processors configured to:
      receive, from a remote computing device, while a do not disturb feature of the computing device is active at the computing device, a request to establish a communication session with the remote computing device and contextual information indicative of an urgency level of the communication session;
      determine, based at least in part on the contextual information indicative of the urgency level of the communication session, to bypass the do not disturb feature of the computing device; and
      in response to determining to bypass the do not disturb feature of the computing device, output, at the one or more output devices, the contextual information indicative of the urgency level of the communication session and at least one of: haptic output or an audible alert that indicates the request to establish the communication session.

12. The computing device of claim 11, wherein to determine whether to bypass the do not disturb feature of the computing device, the one or more processors are further configured to:
compare the urgency level of the communication session with an urgency level threshold associated with a do not disturb exception to determine whether to bypass the do not disturb feature of the computing device.

13. The computing device of claim 12, wherein the one or more processors are further configured to:
in response to determining to bypass the do not disturb feature of the computing device, output, at the one or more output devices, an indication of the request to establish the communication session that indicates at least the urgency level of the communication session.

14. The computing device of claim 11, wherein the urgency level of the communication session is based at least in part on health parameters of a user, wherein the user uses the remote computing device or is another person.

15. The computing device of claim 14, wherein the health parameters of the user include one or more of: a stress level of the user, a blood pressure of the user, a heart rate of the user, an oxygen saturation level of the user, or a blood glucose level of the user.

16. The computing device of claim 14, wherein the urgency level of the communication session is based at least in part on corresponding urgency levels of the health parameters of the user.

17. The computing device of claim 11, wherein the urgency level of the communication session is determined based at least in part on one or more critical events associated with a user of the remote computing device.

18. One or more non-transitory computer-readable storage media comprising instructions stored thereon that, when executed, cause one or more processors of a computing device to:
receive, from a remote computing device, while a do not disturb feature of the computing device is active at the computing device, a request to establish a communication session with the remote computing device and contextual information indicative of an urgency level of the communication session;
determine, based at least in part on the contextual information indicative of the urgency level of the communication session, to bypass the do not disturb feature of the computing device; and
in response to determining to bypass the do not disturb feature of the computing device, output, at one or more output devices, the contextual information indicative of the urgency level of the communication session and at least one of: haptic output or an audible alert that indicates the request to establish the communication session.

* * * * *